US008440402B2

(12) United States Patent
Mass

(10) Patent No.: US 8,440,402 B2
(45) Date of Patent: *May 14, 2013

(54) GENE DETECTION ASSAY FOR IMPROVING THE LIKELIHOOD OF AN EFFECTIVE RESPONSE TO A HER2 ANTIBODY CANCER THERAPY

(75) Inventor: Robert D. Mass, Mill Valley, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/323,322

(22) Filed: Dec. 12, 2011

(65) Prior Publication Data

US 2012/0093838 A1 Apr. 19, 2012

Related U.S. Application Data

(63) Continuation of application No. 11/690,304, filed on Mar. 23, 2007, now Pat. No. 8,076,066, which is a continuation of application No. 09/863,101, filed on May 18, 2001, now abandoned.

(60) Provisional application No. 60/205,754, filed on May 19, 2000.

(51) Int. Cl.
*C12Q 1/68* (2006.01)
*G01N 33/574* (2006.01)

(52) U.S. Cl.
USPC ............................ 435/6.1; 435/7.23

(58) Field of Classification Search .................. None
See application file for complete search history.

(56) References Cited

U.S. PATENT DOCUMENTS

| | | | |
|---|---|---|---|
| 4,753,894 A | 6/1988 | Frankel |
| 4,935,341 A | 6/1990 | Bargmann |
| 4,943,533 A | 7/1990 | Mendelsohn |
| 4,968,603 A | 11/1990 | Slamon |
| 4,975,278 A | 12/1990 | Senter |
| 5,169,774 A | 12/1992 | Frankel |
| 5,183,884 A | 2/1993 | Kraus |
| 5,288,477 A | 2/1994 | Bacus |
| 5,359,046 A | 10/1994 | Capon |
| 5,367,060 A | 11/1994 | Vandlen |
| 5,401,638 A | 3/1995 | Carney |
| 5,464,751 A | 11/1995 | Greene |
| 5,480,968 A | 1/1996 | Kraus |
| 5,514,554 A | 5/1996 | Bacus |
| 5,571,894 A | 11/1996 | Wels |
| 5,578,482 A | 11/1996 | Lippman |
| 5,587,458 A | 12/1996 | King |
| 5,604,107 A | 2/1997 | Carney |
| 5,641,869 A | 6/1997 | Vandlen |
| 5,663,144 A | 9/1997 | Greene |
| 5,677,165 A | 10/1997 | de Boer |
| 5,677,171 A | 10/1997 | Hudziak |
| 5,705,157 A | 1/1998 | Greene |
| 5,720,937 A | 2/1998 | Hudziak |
| 5,720,954 A | 2/1998 | Hudziak |
| 5,725,856 A | 3/1998 | Hudziak |
| 5,726,023 A | 3/1998 | Cheever |
| 5,728,687 A | 3/1998 | Bissery |
| 5,736,137 A | 4/1998 | Anderson |
| 5,747,261 A | 5/1998 | King |
| 5,770,195 A | 6/1998 | Hudziak |
| 5,772,997 A | 6/1998 | Hudziak |
| 5,776,427 A | 7/1998 | Thorpe |
| 5,783,186 A | 7/1998 | Arakawa |
| 5,783,404 A | 7/1998 | Koski |
| 5,801,005 A | 9/1998 | Cheever |
| 5,804,396 A | 9/1998 | Plowman |
| 5,821,337 A | 10/1998 | Carter |
| 5,824,311 A | 10/1998 | Greene |
| 8,824,311 | 10/1998 | Greene |
| 5,834,229 A | 11/1998 | Vandlen |
| 5,837,243 A | 11/1998 | Deo |
| 5,837,523 A | 11/1998 | Greene |
| 5,840,525 A | 11/1998 | Vandlen |
| 5,846,538 A | 12/1998 | Cheever |
| 5,846,749 A | 12/1998 | Slamon |
| 5,856,089 A | 1/1999 | Wang |
| 5,856,110 A | 1/1999 | Vandlen |
| 5,859,206 A | 1/1999 | Vandlen |
| 5,869,445 A | 2/1999 | Cheever |
| 5,876,712 A | 3/1999 | Cheever |
| 5,877,305 A | 3/1999 | Huston |
| 5,908,835 A | 6/1999 | Bissery |
| 5,910,486 A | 6/1999 | Curiel |
| 5,922,845 A | 7/1999 | Deo |
| 5,925,519 A | 7/1999 | Jensen |
| 5,939,531 A | 8/1999 | Wels |
| 5,968,511 A | 10/1999 | Akita |
| 5,977,322 A | 11/1999 | Marks |

(Continued)

FOREIGN PATENT DOCUMENTS

| | | |
|---|---|---|
| EP | 412116 | 4/1989 |
| EP | 332865 | 9/1989 |

(Continued)

OTHER PUBLICATIONS

Sneige et al, 2000 Annual Meeting United States and Canadian Academy of Pathology, Mar. 25-31, 2000, abstract #258 on p. 47A.*

(Continued)

*Primary Examiner* — Laura B Goddard
(74) *Attorney, Agent, or Firm* — Diane Marschang; Ginger R. Dreger; Arnold & Porter LLP

(57) ABSTRACT

The invention provides a method for more effective treatment of patients susceptible to or diagnosed with tumors overexpressing HER2, as determined by a gene amplification assay, with a HER2 antibody. Such method comprises administering a cancer-treating dose of the HER2 antibody, preferably in addition to chemotherapeutic agents, to a subject in whose tumor cells her2 has been found to be amplified e.g., by fluorescent in situ hybridization.

6 Claims, No Drawings

U.S. PATENT DOCUMENTS

| | | | |
|---|---|---|---|
| 5,985,553 | A | 11/1999 | King |
| 5,994,071 | A | 11/1999 | Ross |
| 6,015,567 | A | 1/2000 | Hudziak |
| 6,028,059 | A | 2/2000 | Curiel |
| 6,054,297 | A | 4/2000 | Carter |
| 6,054,561 | A | 4/2000 | Ring |
| 6,096,873 | A | 8/2000 | Schaefer |
| 6,123,939 | A | 9/2000 | Shawver |
| 6,165,464 | A | 12/2000 | Hudziak |
| 6,270,765 | B1 | 8/2001 | Deo |
| 6,333,348 | B1 | 12/2001 | Vogel |
| 6,358,682 | B1 | 3/2002 | Jaffee |
| 6,387,371 | B1 | 5/2002 | Hudziak |
| 6,395,272 | B1 | 5/2002 | Deo |
| 6,399,063 | B1 | 6/2002 | Hudziak |
| 6,403,630 | B1 | 6/2002 | Danenberg |
| 6,407,213 | B1 | 6/2002 | Carter |
| 6,458,356 | B1 | 10/2002 | Arakawa |
| 6,512,097 | B1 | 1/2003 | Marks |
| 6,573,043 | B1 | 6/2003 | Cohen |
| 6,582,919 | B2 | 6/2003 | Danenberg |
| 6,602,670 | B2 | 8/2003 | Daneberg |
| 6,627,196 | B1 | 9/2003 | Baughman |
| 6,632,979 | B2 | 10/2003 | Erickson |
| 6,719,971 | B1 | 4/2004 | Carter |
| 6,800,738 | B1 | 10/2004 | Carter et al. |
| 6,984,494 | B2 | 1/2006 | Ralph |
| 7,018,809 | B1 | 3/2006 | Carter |
| 7,097,840 | B2 | 8/2006 | Erickson et al. |
| 7,129,051 | B2 | 10/2006 | Cohen et al. |
| 7,279,287 | B2 | 10/2007 | Ralph |
| 7,371,376 | B1 | 5/2008 | Fendly |
| 7,371,379 | B2 | 5/2008 | Baughman et al. |
| 2002/0001587 | A1 | 1/2002 | Erickson et al. |
| 2002/0031515 | A1 | 3/2002 | Caligiuri |
| 2002/0035736 | A1 | 3/2002 | Erickson et al. |
| 2002/0051785 | A1 | 5/2002 | Salmon |
| 2002/0064785 | A1 | 5/2002 | Mass |
| 2002/0076408 | A1 | 6/2002 | Buchsbaum |
| 2002/0076695 | A1 | 6/2002 | Ross |
| 2002/0090662 | A1 | 7/2002 | Ralph |
| 2002/0141993 | A1 | 10/2002 | Ashkenazi |
| 2002/0142328 | A1 | 10/2002 | Danenberg |
| 2002/0155527 | A1 | 10/2002 | Stuart |
| 2002/0173629 | A1 | 11/2002 | Jakobovits et al. |
| 2002/0192211 | A1 | 12/2002 | Hudziak |
| 2002/0192652 | A1 | 12/2002 | Danenberg |
| 2003/0022918 | A1 | 1/2003 | Horak |
| 2003/0059790 | A1 | 3/2003 | Jaffee |
| 2003/0103973 | A1 | 6/2003 | Rockwell |
| 2003/0108545 | A1 | 6/2003 | Rockwell |
| 2003/0134344 | A1 | 7/2003 | Mass |
| 2003/0144252 | A1 | 7/2003 | Furr |
| 2003/0147884 | A1 | 8/2003 | Paton et al. |
| 2003/0152987 | A1 | 8/2003 | Cohen |
| 2003/0157097 | A1 | 8/2003 | Noguchi et al. |
| 2003/0170234 | A1 | 9/2003 | Hellmann |
| 2003/0190689 | A1 | 10/2003 | Crosby |
| 2003/0211530 | A1 | 11/2003 | Danenberg |
| 2003/0228663 | A1 | 12/2003 | Lowman et al. |
| 2004/0037823 | A9 | 2/2004 | Paton |
| 2004/0106161 | A1 | 6/2004 | Bossenmaier et al. |
| 2005/0100944 | A1 | 5/2005 | Cohen et al. |
| 2005/0208043 | A1 | 9/2005 | Adams et al. |
| 2005/0238640 | A1 | 10/2005 | Sliwkowski |
| 2005/0244929 | A1 | 11/2005 | Carter |
| 2006/0013819 | A1 | 1/2006 | Kelsey |
| 2006/0034842 | A1 | 2/2006 | Adams et al. |
| 2006/0046270 | A1 | 3/2006 | Ralph |
| 2006/0067930 | A1 | 3/2006 | Adams et al. |
| 2006/0073143 | A1 | 4/2006 | Adams et al. |
| 2006/0121044 | A1 | 6/2006 | Amler et al. |
| 2006/0198843 | A1 | 9/2006 | Adams et al. |
| 2006/0204505 | A1 | 9/2006 | Sliwkowski |
| 2006/0210561 | A1 | 9/2006 | Baughman et al. |
| 2006/0228745 | A1 | 10/2006 | Mass |
| 2006/0275305 | A1 | 12/2006 | Bryant |
| 2007/0009976 | A1 | 1/2007 | Lenz et al. |
| 2007/0020261 | A1 | 1/2007 | Sliwkowski |
| 2007/0037228 | A1 | 2/2007 | Moecks et al. |
| 2007/0292419 | A1 | 12/2007 | Hellmann |
| 2008/0038271 | A1 | 2/2008 | Amler et al. |
| 2008/0050373 | A1 | 2/2008 | Cohen |
| 2008/0050385 | A1 | 2/2008 | Friess et al. |
| 2008/0102069 | A1 | 5/2008 | Friess et al. |
| 2008/0108096 | A1 | 5/2008 | Ralph |
| 2008/0112957 | A1 | 5/2008 | Fendly et al. |
| 2008/0112958 | A1 | 5/2008 | Mass |

FOREIGN PATENT DOCUMENTS

| | | |
|---|---|---|
| EP | 494135 | 9/1989 |
| EP | 444181 | 8/1990 |
| EP | 1006194 | 8/1990 |
| EP | 502812 | 1/1992 |
| EP | 554441 | 8/1992 |
| EP | 656367 | 8/1992 |
| EP | 616812 | 3/1993 |
| EP | 599274 | 11/1993 |
| EP | 711565 | 11/1995 |
| JP | 3-240498 | 10/1991 |
| JP | 5-117165 | 5/1993 |
| JP | 5-170667 | 7/1993 |
| JP | 5-213775 | 8/1993 |
| JP | 2761543 B2 | 6/1998 |
| JP | 2895105 B2 | 5/1999 |
| WO | WO 87/07646 A2 | 12/1987 |
| WO | WO 89/06692 | 7/1989 |
| WO | WO 89/10412 | 11/1989 |
| WO | WO 90/14357 | 11/1990 |
| WO | WO 91/02062 | 2/1991 |
| WO | WO 91/05264 | 4/1991 |
| WO | WO 92/10573 | 6/1992 |
| WO | WO 92/20798 | 11/1992 |
| WO | WO 93/03741 | 3/1993 |
| WO | WO 93/12220 | 6/1993 |
| WO | WO 93/16185 | 8/1993 |
| WO | WO 93/21232 | 10/1993 |
| WO | WO 93/21319 | 10/1993 |
| WO | WO 94/00136 | 1/1994 |
| WO | WO 94/22478 | 10/1994 |
| WO | WO 94/28127 | 12/1994 |
| WO | WO 95/16051 | 6/1995 |
| WO | WO 95/17507 | 6/1995 |
| WO | WO 95/28485 | 10/1995 |
| WO | WO 96/07321 | 3/1996 |
| WO | WO 96/16673 | 6/1996 |
| WO | WO 96/18409 | 6/1996 |
| WO | WO 96/40789 | 12/1996 |
| WO | WO 97/00271 | 1/1997 |
| WO | WO 97/04801 | 2/1997 |
| WO | WO 97/20858 | 6/1997 |
| WO | WO 97/27848 | 8/1997 |
| WO | WO 97/35885 | 10/1997 |
| WO | WO 97/38731 | 10/1997 |
| WO | WO 98/02463 | 1/1998 |
| WO | WO 98/02540 | 1/1998 |
| WO | WO 98/02541 | 1/1998 |
| WO | WO 98/17797 | 4/1998 |
| WO | WO 98/18489 | 5/1998 |
| WO | WO 98/33914 | 8/1998 |
| WO | WO 98/45479 | 10/1998 |
| WO | WO 99/31140 | 6/1999 |
| WO | WO 99/39729 | 8/1999 |
| WO | WO 99/48527 | 9/1999 |
| WO | WO 99/55367 | 11/1999 |
| WO | WO 00/20641 | 4/2000 |
| WO | WO 00/61145 | 10/2000 |
| WO | WO 00/61185 | 10/2000 |
| WO | WO 00/69460 | 11/2000 |
| WO | WO 00/78347 | 12/2000 |
| WO | WO 01/00238 | 1/2001 |
| WO | WO 01/00244 | 1/2001 |
| WO | WO 01/00245 | 1/2001 |
| WO | WO 01/05425 | 1/2001 |
| WO | WO 01/09187 | 2/2001 |
| WO | WO 01/15730 | 3/2001 |
| WO | WO 01/20033 | 3/2001 |

| | | |
|---|---|---|
| WO | WO 01/21192 | 3/2001 |
| WO | WO 01/32155 | 5/2001 |
| WO | WO 01/34574 | 5/2001 |
| WO | WO 01/53354 | 7/2001 |
| WO | WO 01/56604 | 8/2001 |
| WO | WO 01/64246 | 9/2001 |
| WO | WO 01/76586 | 10/2001 |
| WO | WO 01/76630 | 10/2001 |
| WO | WO 01/87334 | 11/2001 |
| WO | WO 01/87336 | 11/2001 |
| WO | WO 01/89566 | 11/2001 |
| WO | WO 02/05791 | 1/2002 |
| WO | WO 02/09754 | 2/2002 |
| WO | WO 02/11677 | 2/2002 |
| WO | WO 02/44413 | 6/2002 |
| WO | WO 02/45653 | 6/2002 |
| WO | WO 02/055106 | 7/2002 |
| WO | WO 03/087131 | 10/2003 |
| WO | WO 2004/008099 A2 | 1/2004 |
| WO | WO 2005/117553 | 12/2005 |
| WO | WO 2006/007398 A1 | 6/2006 |
| WO | WO 2006/063042 A2 | 6/2006 |
| WO | WO 2006/078307 A1 | 7/2006 |
| WO | WO 2006/091693 | 8/2006 |
| WO | WO 2006/096861 | 9/2006 |
| WO | WO 2006/107854 A2 | 10/2006 |
| WO | WO 2007/003420 | 1/2007 |
| WO | WO 2007/013950 | 2/2007 |
| WO | WO 2007/019899 | 9/2007 |
| WO | WO 2007/107329 | 9/2007 |
| WO | WO 2007/145862 | 12/2007 |
| WO | WO 2008/031531 | 3/2008 |

OTHER PUBLICATIONS

"Could Medarex's MAb be prostate cancer's Herceptin?" Scrip 2442:25, (Jun. 2, 1999).
Aasland et al., "Expression of Oncogenes in Thyroid Tumours: Coexpression of c-erbB2/neu and c-erbB", British Journal of Cancer 57(4): 358-363, (1988).
Agus at al., "Differential Anti-Tumor Effects of Targeting Distinct Epitopes of the Her-2/neu extracellular Domain in Xenograft Models of Prostate Cancer.", Proceedings of the American Association, for Cancer Research Annual Meeting (Abstract #4570) 41:719 (Mar. 2000).
Agus et al., "Response of Prostate Cancer to Anti-Her-2/neu Antibody in Androgen-Dependent and-Independent Human Xenograft Models", Cancer Research 59: 4761-4764, (1999).
Agus et al., "Targeting ligand-activated BrbB2 signaling inhibits breast and prostate tumor growth", Cancer Cell 2(2): 127-137, (2002).
Akiyama et al., "Tumor Promoter and Epidermal Growth Factor Stimulate Phosphorylation of the c-erbB-2 Gene Product in MKN-7 Human Adenocarcinoma Cells" Molecular & Cellular Biology 8(3): 1019-1026, (Mar. 1988).
Anastasi et al, "Detection of Trisomy 12 in Chronic Lymphocytic Leukemia by Fluorescence In Situ Hybridization to Interphase Cells: A Simple and Sensitive Method", Blood 79(7):1796-1801, (1992).
Anastasi et al., "Cytogenetic Clonality in Myelodysplastic Syndromes Studied With Fluorescence In Situ Hybridization: Lineage, Response To Growth Factor Therapy, and Clone Expansion", Blood 81(6): 1580-1585, (Mar. 15, 1993).
Anastasi et al., "Direct Correlation of Cytogenetic Findings With Cell Morphology Using In Situ Hybridization: An Analysis of Suspicious Cells,in Bone Marrow Specimens of Two Patients. Completing Therapy for Acute Lymphoblastic Leukemia" Blood 77(11):2456-2462 (Jun. 1, 1991).
Arteaga et al., "p185n¯cerne$^{-4}$ Signaling Enhances Cisplatin-induced Cytotoxicity in Human Breast Carcinoma Cells: Association Between an Oncogenic Receptor Tyrosine Kinase and Drug-induced DNA Repair", Cancer Research 54(14): 3758-3765, (Jul. 15, 1994).
Bacus et al., "Differentiation of Cultured Human Breast Cancer Cells (AU-565 and MCF-7) Associated With Loss of Cell Surface HER-2/neu Antigen" Molecular Carcinogenesis 3(6):350-362 (1990).
Bacus et al., "Tumor-inhibitory Monoclonal Antibodies to the HER-2/Neu Receptor Induce Differentiation of Human Breast Cancer Cells" Cancer Research 52(9): 2580-2589, (1992).
Baselga and Mendelsohn, "Receptor Blockade With Monoclonal Antibodies As Anti-Cancer Therapy" Pharmac. Ther. 64: 127-154, (1994).
Baselga et al., "Monoclonal Antibodies Directed Against Growth Factor Receptors Enhance the Efficacy of Chemotherapeutic Agents." Annals of Oncology (abstract #010) 5(Suppl. 5) (1994).
Baselga et al., "Anti HER2 Humanized Monoclonal Antibody (MAb) Alone and in Combination with Chemotherapy Against Human Breast Carcinoma Xenografts" Proceedings of ASCO—13th Annual Meeting (Abstract #53), Dallas, TX 13:63, (Mar. 1994).
Baselga et al., "HER2 Overexpression and Paclitaxel Sensitivity in Breast Cancer: Therapeutic Implications" Oncology (Supplement No. 2) 11(3): 43-48 (Mar. 1997).
Baselga et al., "Phase II Study of Weekly Intravenous Recoinnant Humanized Anti-p185 a-ha-d Monoclonal Antibody in Patients With HER2/neu-Overexpressing Metastatic Breast Cancer" J. Clin. Oncol. 14(3):737-744 (Mar. 1996).
Baselga et al., "Phase II study of weekly intravenous trastnzumab (Herceptin) in patients with HER2/neu-overexpressing metastatic breast cancer" Seminars in Oncology 26(4 Suppl 12): 78-83, (1999).
Baselga et al., "Recombinant Humanized Anti-HER2 Antibody (Herceptin) Enchances the Antitumor Activity of Paclitaxel and Doxorubicin against HER2/neu Overexpressing Human Breast Cancer Xenografts", Cancer Research 58: 2825-2831 (Jul. 1998).
Borst et al., "Oncogene Alterations in Endometrial Carcinoma", Gynecologic Oncology 38(3): 364-366, (1990).
Brady et al., "Iodine125 labeled anti-epidermal growth factor receptor-425 in the treatment of malignant astrocytomas. A pilot Study" Journal of Neurosurgical Sciences 34(3-4):243-249 (Jul.-Dec. 1990).
Burden and Yarden., "Neuregulins and Their Receptors: A Versatile signaling Module in Organogenesis and Oncogenesis." Neuron 18(6): 847-855, (Jun. 1997).
Burris III, H., "Docetaxel (Taxotere) in HER-2-positive patients and in combination with trastuzumab (Herceptin)", Seminars in Oncology 27(2 Suppl 3):19-23, (Apr. 2000).
Cappuzzo et al., "Epidermal growth factor receptor gene and protein and gefitinib sensitivity in non-small-cell lung cancer" Journal of the National Cancer Institute 97(9): 643-655, (May 4, 2005).
Carlson et al., "HER2 testing in breast cancer: NCCN Task Force report and recommendations", Journal of the National Comprehensive Cancer Network 4(Suppl 3):S1-S24, (2006).
Carraway and Cantley, "A Neu Acquaintance for ErbB3 and ErbB4: A Role for Receptor Heterodimerization in Growth Signaling" Cell 78: 5-8, (Jul. 15, 1994).
Carraway et al., "Neuregulin-2, A New Ligand of ErbB3/ErbB4-Receptor Tyrosine Kinases", Nature 387: 512-516, (May 1997).
Carter et al., "Humanization of an Anti-p185HERA Antibody for Human Cancer Therapy", Proc. Natl. Acad. Sci. USA 89(10): 4285-4289, (May 1992).
Chang et al., "Ligands for ErbB-Family Receptors Encoded by a Neuregulin-Like Gene", Nature 387: 509-512, (1997).
Choong et al., "Gelltinib response of erlotinib-refractory lung cancer involving meninges—role of EGFR mutation" Nature Clinical Practice Oncology 3(1): 50-57, (2006).
Clark, Gary M. et al., "Follow-up Study of HER-2/neu Amplification in Primary Breast Cancer", Cancer Research, 51, 944-948, Feb. 1, 1991.
Cobleigh et al., "Multinational study of the efficacy and safety of humanized anti-HER2 monoclonal antibody in women who have HER2-overexpressing metastatic breast cancer that has progressed after chemotherapy for metastatic disease" Journal of Clinical Oncol 17(9):2639-2648 (Sep. 1999).
Cohen et al., "Expression Pattern of the neu NGL Gene-Encoded Growth Factor Receptor Protein (p185neu) in Normal and Transformed Epithelial Tissues of the Digestive Tract" Oncogene 4(1): 81-88, (1989).
Connelly and Stern., "The Epidermal Growth Factor Receptor and the Product of the neu Protooncogene Are Members of a Receptor Tyrosine Phosphorylation Cascade." Proc. Natl. Acad. Sci. USA 87: 6054-6057, (1990).

Couturier et al (Mod Pathol, 2000, 13:1238-1243).

Craft et al., "A Mechanism for Hormone-Independent Prostate Cancer Through Modulation of Androgen Receptor Signaling by the HER-2/neu Tyrosine Kinase." Nature Medicine 5(3):280-285 (Mar. 1999).

Dacic et al., "Significance of EGFR protein expression and gene amplification in non-small cell lung carcinoma" American Journal of Clinical Pathology 125(6): 860-865, (2006).

DakoCytomation, "Herceptest TM for immunocytochemicaf staining" (package insert) pp. 1-25 (2004).

De Santes et al., "Raido labeled Antibody Targeting of the HER-2/neu Oncoprotein" Cancer Research 52: 1916-1923 (1992).

Di Fiore et al., "erbB-2 is a Potent Oncogene When Overexpressed in NIH/3T3 Cells.", Science 237(4811):178-182, (Jul. 10, 1987).

Drebin et al., "Down-Modulation of an Oncogene Protein Product and Reversion of the Transformed Phenotype by Monoclonal Antibodies", Cell, vol. 41, pp. 695-706 (1985).

Drebin et al., "Monoclonal Antibodies Reactive with Distinct Domains of the neu Oncogene-Encoded p185 Molecule Exert Synergistic Anti-tumor Effects in Vivo", Oncogene, vol. 2, pp. 273-277 (1988).

Drebin et al., "Monoclonal Antibodies Specific for the neu Oncogene Product Directly Mediate Anti-tumor Effects In Vivo" Oncogene 2(4): 387-394, (1988).

Drebin et al., Inhibition of Tumor Growth by a Monoclonal Antibody Reactive With an Oncogene-Encoded Tumor Antigen Proc. Natl. Acad. Sci. 83: 9129-9133 (Dec. 1986).

Dressler et al., "Amplification of ErbB2 by Fluorescent In Situ Hybridization (FISH): An Alternate Method to Predict Outcome Following Dose-Escalated CAF in Stage II, Node Positive Breast Cancer Patients." Proc. Annual Meet. Amer. Soc. Clin. Oncol. (Meeting Abstract) 18:A281 (1999).

D'Souza et al., "Overexpression of ERBB2 in Human Mammary Epithelial Cells Signals Inhibition of Transcription of the E-cadherin Gene", Proc. Natl. Acad. Sci., USA, vol. 91, pp. 7202-7206 (1994).

Earp et al., "Heterodimerization and Functional Interaction Between MP Receptor Family Members: A New Signaling Paradigm With. Implications for Breast Cancer Research", Breast Cancer Res and Treatment 35: 115-132 (1995).

FDA Clinical Review of BLA 98-0369 Herceptin, Trastuzumab (rhuMAb HER2), Date of Approval: Sep. 25, 1998, (pp. 1-99).

Fendly, B.M. et al., "Characterization of Murine Monoclonal Antibodies Reactive to Either the Human Epidermal Growth Factor Receptor or HER2/neu Gene Product" Cancer Research 50: 1550-1558, (1990).

Fleiss, JL Statistical Methods for Rates and Proportions, $2^{nd}$ edition, New York, NY: Wiley pp. 13-17, (1981).

Fukushige et al., "Localization of a Novel v-erbB-Related Gene, c-erbB-2, on Human Chromosome 17 and its Amplification in a Gastric Cancer Cell Line", Molecular and Cellular Biology, vol. 6, No. 3, pp. 955-958 (1986).

Gemzar (gemcitabine HCL), "Product Information—PDR" (2000).

Goldenberg, M., "Trastuzumab, a Recombinant DNA-Derived Humanized Monoclonal Antibody, a Novel Agent for the Treatment of Metastatic Breast Cancer" Clinical Therapeutics 21(2):309-316 (1999).

Goldman et al., Heterodimerization of the erbB-1 and erbB-2 Receptors in Human Breast Carcinoma Cells: A Mechanism for Receptor Transregulation Biochemistry 29(50):11024-11028, (1990).

Graus-Porta at al., "ErbB-2, The Preferred Heterodimerization Partner of All ErbB Receptors, is a Mediator of Lateral Signaling." EMBO Journal 16(7): 1647-1655, (1997).

Green et al., "Preclinical Evaluation of WR-151327: An Orally Active Chemotherapy Protector", Cancer Research 54(3): 738-741 (Feb. 1, 1994).

Groenen et al., "Structure-Function Relationships for the EGF/TGF-a Family of Mitogens", Growth Factors 11: 235-257, (1994).

Gu et al., "Overexpression of her-2/neu in Human Prostate Cancer and Benign Hyperplasia", Cancer Letters, vol. 99, pp. 185-189 (1996).

Guerin et al., "Overexpression of Either c-myc or c-erbB-2/neu Proto-Oncogenes in Human Breast Carcinomas: Correlation with Poor Prognosis" Oncogene Research, vol. 3, pp. 21-31 (1988).

Guy et al., "Expression of the neu Protooncogene in the Mammary Epithelium of Transgenic Mice Induces Metastatic Disease." Proc. Natl. Acad. Sol. USA 89(22): 10578-10582, (Nov. 15, 1992).

Hancock, M.C. et al., A Monoclonal Antibody Against the c-erbB-2 Protein Enhances the Cytotoxicity of cis-Diamminedichloroplatinum Against Human Breast and Ovarian Tumor Cell Lines:, vol. 51, pp. 4575-4580 (1991).

Harari at al., "Neuregulin-4: A. Novel Growth Factor That Acts Through the ErbB-4 Receptor Tyrosine Kinase" Oncogene 18: 2681-2689 (1999).

Harweth et al., "Monoclonal Antibodies Against the Extracelluler Domain of the erbB-2 Receptor Function as Partial Ligand Agonists", The Journal of Biological Chemistry, vol. 267, No. 21, pp. 15160-15167 (1992).

Herceptin 150 mg Powder for concentrate for solution for infusion, Approved label from UK Medicines Agency, pp. 1-28.

Hirsch and Bunn Jr., "Epidermal growth factor receptor inhibitors in lung cancer: smaller or larger molecules, selected or unselected populations?" Journal of Clinical Oncology 23(36):9044-9047, (2005).

Hirsch et al., "Epidermal growth factor receptor in non-small-cell lung carcinomas: correlation between gene copy number and protein expression and impact on prognosis", Journal of Clinical Oncology 21(20): 3798-3807 (Oct. 15, 2003).

Hirsch et al., "Increased epidermal growth factor receptor gene copy number detected by fluorescence in situ hybridization associates with increased sensitivity to gefitinib in patients with bronchioloalveolar carcinoma subtypes: a Southwest Oncology Group Study" J Clin Oncol 23:6838-6845 (2005).

Holmes et al., "Identification of Heregulin, A Specific Activator of $p185erns^2$" Science 256: 1205-1210, (1992).

Hudziak et al., "Increased Expression of the Putative Growth Factor Receptor p185E-$k^4$ Causes Transformation and Tumorigenesis of NTH 3T3 Cells" Proc. Nat': Acad. gci. USA 84(20):7159-7163, (1987).

Hudziak et al., "$p185^{HER2}$ Monoclonal Antibody has Antiproliferative Effects in Vitro Effects in Vitro and Sensitizes Huamn Breast Tumor Cells to Tumor Necrosis Factor", Molecular and Cellular Biology, vol. 9, No. 3, pp. 1165-1172 (1989).

Hynes and Stern, "The Biology of erbB-2/neu/HER-2 and Its Role in•Cancer" Biochimica et Biophysica Acta 1198(2-3): 165-184, (Dec. 30, 1994).

Ilgen et al., "Characterization of anti-BER/2 antibodies which inhibit the growth of breast tumor cells in vitro" Proceedings of the American Association for Cancer Research (abstract #3209) 37:470 (Mar. 1996).

Jacobs et al., "Comparison of fluorescence in situ hybridization and immunohistochemistry for the evaluation of HER-2/neu in breast cancer" Journal of Clinical Oncology 17(7): 1974-1982, (1999).

James et al., "Phase II. Trial of the Bispecific Antibody MDX-H210 (anti-Her2/Neu X-anti-CD64) Combined With GM-CSF in Patients With Advanced Prostate and Renal Cell Carcinoma That Express Her2/Neu." British Journal of Cancer (Abstract #56) 78:19 (1998).

Johns et al., "The antitumor monoclonal antibody 806 recognizes a high-mannose form of the EGF receptor that reaches the cell surface when cells over-express the receptor", FASEB Journal (Express article 10.1096/fj.04-1766fje published online.) pp. 1-18 (Mar. 17, 2005).

Jones et al., "Binding Interaction of the Heregulinβ egf Domain with ErbB3 and ErbB4 Receptors Assessed by Alanine Scanning Mutagenesis" Journal of Biological Chemistry 273(19):11667-11674, (1998).

Kannan at al., "Cripto Enhances the Tyrosine Phosphorylation of Shc and Activates Mitogen-activated Protein Kinase (Mum) in Mammary Epithelial Cells" Journal of Biological Chemistry 272(6): 3330-3335, (1997).

Karunagaran et al., "ErbB-2 is a Common Auxiliary Subunit of NDF and EGF Receptors: Implications for Breast Cancer" EMBO Journal 15(2): 254-264 (1996).

Kasprzyk et al., "Therapy of an Animal Model of Human Gastric Cancer Using a Combination of Anti-erbB-2 Monoclonal Antibodies" Cancer Research 52(10): 2771-2776 (May 15, 1992).

Kern et al., "p185neu Expression in Human Lung Adenocarcinomas Predicts Shortened Survival", Cancer Research—50(16): 5184-5191, (Aug. 15, 1990).

Kersting et al., "Amplifications of the epidermal growth factor receptor gene (egfr) are common in phyllodes tumors of the breast and are associated with tumor progression" Laboratory Investigation 86(1): 54-61 (Jan. 2006).

King et al., "Amplification of a Novel v-erbB-Related Gene in a Human Mammary Carcinoma", Science, 229: 974-976, (Sep. 1985).

King et al., TEGF Binding to its Receptor Triggers a Rapid Tyrosine Phosphorylation of the erbB-2 Protein in the Mammary Tumor Cell Line SK-BR-3. EMBO Journal 7(6):1647-1651, (1988).

Klapper et al., "A Subclass of Tumor-Inhibitory Monoclonal Antibodies to ErbB-2/HER2 Blocks Crosstalk With Growth Factor Receptors" Oncogene 14: 2099-2109 (1997).

Kobayashi et al., "EGER mutation and resistance of non-small-cell lung cancer to gefitinib", New England U. of Medicine 352(8): 786-792, (2005).

Kokai et al., "Synergistic Interaction of p185c-neu and the EGF Receptor Leads to Transformation of Rodent Fibroblasts" Cell 58: 287-292 (Jul. 28, 1989).

Kotts et al., "Differential Growth Inhibition of Human Carcinoma Cells Exposed to Monoclonal Antibodies Directed against the Extracellular Domain of the HER2/ERBB2 Protooncogene", In Vitro (Abstract #176) 26(3):59A (1990).

Kotts et al., "GroWS7AMilOn of Human Breast Carcinoma Cells Exposed to Combinations of Interferon-gamma and Monoclonal Antibodies Directed against the Extracellular Domain of the HER2/ERBB2 Protooncogene" (Program 1470, Joint Mtg of ASBMB & AAI in New Orleans, LA on Jun. 4-7, 1990 poster).

Kotts et al., "Growth Inhibition of Human Breast Carcinoma Cells Exposed to Combinations of Interferon-Gamma and Monoclonal Antibodies Directed Against the Extracellular Domain of the Her2/erbB2 Oncogene Protein" FASEB Journal (abstract #1470) 4(7);A1946 (1990).

Kraus et al., "Isolation and Characterization of ERBB3, A Third Member of the ERBB/Epidermal Growth Factor Receptor Family: Evidence for Overexpression in a Subset of Human Mammary Tumors" Proc. Natl Acad. Sci. USA 86:9193-9197 (Dec. 1989).

Kumar et al., "Regulation of Phosphorylation of the c-erbB-2/HER2 Gene Product by a Monoclonal Antibody and Serum Growth Factor(s) in Human Mammary Carcinoma Cells", Molecular & Cellular Biology 11(2):979-986, (1991).

Kuter, I., "Breast cancer" The Oncologist 6(4):338-346 (2001).

Lee et al., "Transforming Growth Factor C(: Expression, Regulation, and Biological Activities", Pharmacological Reviews 47(1):51-85 (Mar. 1995).

Lemke,G., "Neuregulins in Development" Molecular and Cellular Neurosciences 7:247-262, (1996).

Leonard et al., "Anti-human epidermal growth tactor receptor 2 monoclonal antibody therapy for breast cancer" British Journal of Surgery 89(3): 262-271 (Mar. 2002).

Levi et al., "The Influence of Heregulins on Human Schwann Cell Proliferation" J. Neuroscience 15(2):1329-1340, (Feb. 1995).

Lewis et al., "Differential Responses of Human Tumor Cell Lines to Anti-p185tusx[4] Monoclonal Antibodies" Cancer Immunol. Immunother. 37:255-263 (1993).

Lewis et al., "Growth Regulation of Human Breast and Ovarian Tumor Cells by Heregulin: Evidence for the Requirement of ErbB2 as a Critical Component in Mediating Heregulin Responsiveness", Cancer Research 56:1457-1465, (Mar. 15, 1996).

Maier et al., "Requirements for the Internalization of a Murine Monoclonal Antibody Directed against the HER-2/neu Gene Product c-erbB-2" Cancer Research 51(19):5361-5369, (1991).

Masui et al., "Growth Inhibition of Human Tumor Cells in Athymic Mice by Anti-Epidermal Growth Factor Receptor Monoclonal Antibodies" Cancer Research 44(3):1002-1007, (1984).

Masuko et al., "A murine Monoclonal Antibody That Recognizes an Extracellular Domain of the Human c-erbB-2 Protooncogene Product" Jpn J. Cancer Res. 80:10-14, (1989).

McCann at al., "Prognostic Significance of c-erbB-2 and Estrogen Receptor Status in Human Breast Cancer", Cancer Research 51(12):3296-3303 (Jun. 15, 1991).

McCann et al., "c-crbB-2 Oncoprotein Expression in Primary Human Tumors" Cancer 65(1):88-92, (1990).

McKenzie et al., "Generation and Characterization of Monoclonal Antibodies Specific for the Human neu Oncogene product, p185" Oncogene 4:543-548 (1989).

MenTilsohn at al., "Receptor Blockade and Chemotherapy: A New Approach to Combination Cancer Therapy." Annals of Oncology (abstract #040) 7(Suppl. 1):22 (1996).

Mitchell, Malcolm S et al., "The Role of Immunohistocheinistry and Fluorescense In Situ Hybridization for HER-2/neu in Assessing the Prognosis of Breast Cancer", Seminars in Oncology, vol. 26, No. 4, Suppl 12, pp. 108-116, (1999).

Modjtahedi et al., "Immunotherapy of human tumour xenografts overexpressing the EGF receptor with rat antibodies that block growth factor-receptor interaction" British Journal of Cancer 67(2): 254-261, (Feb. 1993).

Morrissey at al., "Axon-Induced Mitogenesis of Human Schwann Cells Involves Heregulin and p185$^{erb2}$", Proc. Natl. Acad. Sci. USA 92:1431-1435 (Feb. 1995).

Mrhalova et al., "Epidermal growth factor receptor—its expression and copy numbers of EGFR gene in patients with head and neck squamous cell carcinomas" Neoplasma 52(4): 338-343 (2005).

Myers et al., "Biological Effects of Monoclonal Antireceptor Antibodies Reactive with neu Oncogene Product, p185neu" Methods in Enzymology 198: 277-290 (1991).

Myers et al., "Intracellular antibody mediated down-regulation of ple5ersb-2 expression in malignant prostatic cells" Proceedings of the American Association for Cancer Research Annual Meeting (Abstract #2334) 37: 342, (1996).

Nahta and Esteva, "HER-2-targeted therapy: lessons learned and future directions" Clinical Cancer Research 9(14): 5078-5084, (2003).

Neige, N. et al., "Abstract 258", 2000 Annual Meeting US and Canadian Academy of Pathology Meeting, Mar. 25-31, 2000, New Orleans, LA (2 pgs).

Nelson et al., "Comparison of HER-2/NEU Amplification Using Fluorescent In Situ Hybridization (FISH) with Immunohistochemically Determined Overexpression in Breast Cancers" Modern Pathology (abstract No. 106) 9(1):21A (Jan. 1996).

Norton; L., "Evolving Concepts in the Systemic Drug Therapy of Breast Cancer." Seminars in Oncology 24(4 Suppl 10):510-3-310-10 (Aug. 1997).

Pao et al., "EGF receptor gene mutations are common in lung cancers from "never smokers" and are associated with sensitivity of tumors to gefitinib and erlotinib", Proc. Natl. Acad. Sci. USA 101(36): 13306-13311, (Sep. 7, 2004).

Park et al., "Amplification, Overexpression, and Rearrangement of the erbB-2 Protooncogene in Primary Human Stomach Carcinomas" Cancer Research 49(23): 6605-6609, (Dec. 1, 1989).

Park et al., "EGFR gene and protein expression in breast cancers" Eur. J. Surg. Oncol. in press, doi:10.1016/j.ejso.2007.01.033) pp. 1-5, (2007).

Paterson et al., "Correlation Between c-erbB-2 Amplification and Risk of Recurrent Disease in Node-Negative Breast Cancer" Cancer Research 51(2):556-567 (Jan. 15, 1991).

Pauletti et al., "Detection and quantitation of HER-2/neu gene' amplification in human breast cancer archival material using fluorescence in situ hybridization", Oncogene 13(1):63-72 (Jul. 4, 1996).

Pegram et al., "Inhibitory effects of combinations of HER-2/neu antibody and chemotherapeutic agents used for treatment of human breast cancers" Oncogene 18:2241-2251, (1999).

Pegram et al., "Phase II Study of Receptor-Enhanced Chemosensitivity Using Recombinant Humanized Anti-p185.HER$^2$/neu Monoclonal Antibody Plus Cisplatin in Patients With HER2/neu-Overexpressing Metastatic Breast Cancer Refractory to Chemotherapy Treatment" Journal of Clinical Oncology 16(8): 2659-2671 (1998).

Perrotta and Abuel, "Response of Chronic Relapsing ITP of 10 Years Duration to Rituximab", Blood (Abstract #3360) 92(10 Suppl. 1 Part 1-2):88b (1998).

Persons, et al., "Fluorescence In Situ Hybridfiation (FISH) for Detection of HER-2/neu Amplification in Breast Cancer: A Multicenter Portability Study.", Annals of Clinical and Laboratory Science 30(1): 41-48(Jan. 2000).
Pietras et al., "Antibody to HER-2/neu Receptor Blocks DNA Repair After Cisplatin in Human Breast and Ovarian Cancer Cells" Oncogene 9:1829-1838 (1994).
Plowman et al., "Heregulin Induces Tyrosine Phosphorylation of HER4/p180erraa" Nature (Letters to Nature) 366:473-475 (Dec. 2, 1993).
Plowman et al., "Ligand-Specific Activation of HER4/p180arba[4], A Fourth Member of the Epidermal Growth Factor Receptor Family" Proc. Natl. Acad. Sci. USA 90: 1746-1750, (1993).
Presta et al., Humanization of an Anti-Vascular Endothelial-Growth Factor Monoclonal Antibody for the Therapy of Solid Tumors and Other Disorders Cancer Research 57(20): 4593-4599, (Oct. 15, 1997).
Product Approval Information—Licensing Action, FDA Archive (1 pg), Apr. 13, 2000.
Raefsky et al., "Phase II Trial of Docetaxel and Herceptin as First-or Second-Line Chemotherapy for Women with Metastatic Breast Cancer Whose Tumors Overexpress EER2", Proceedings of ASCO (Abstract ()523) 18:137a (1999).
Ravdin and Chamness, "The c-erbB-2 proto-oncogene as a prognostic and predictive marker in breast cancer: a paradigm for the development of other macromolecular markers—a review" Gene 159(1):19-27 (Jun. 14, 1995).
Riely et al., "Clinical course of patients with non-small cell lung cancer and epidermal growth factor receptor exon 19 and exon 21 mutations treated with gefitinib or erlotinib" Clinical Cancer Research 12(3 Pt 1):839-844, (Feb. 1, 2006).
Ro et al., "Amplified and overexpressed epidermal growth factor receptor gene in uncultured primary human breast carcinoma", Cancer Research 48(1):161-164 (Jan. 1, 1988).
Rodeck et al., "Interactions between growth factor receptors and corresponding monoclonal antibodies in human tumors" J. Cellular Biochem. 35(4): 315-320 (1987).
Ross et al., "HER-2/neu Gene Amplification Status in Prostate Cancer BY Fluorescence in Situ Hybridization" Hum. Pathol. 28(7):827-833 (Jul. 1997).
Ross et al., "Prognostic Significance of HER-2/neu Gene Amplification Status by Fluorescence In Situ Hybridization of Prostate Carcinoma" Cancer 79(11):2162-2170, (Jun. 1, 1997).
Ross, J. and J. Fletcher, "The HER-2/neu Oncogene in Breast Cancer: Prognostic Factor, Predictive Factor, and Target for Therapy." Stem Cells 6(6): 413-428 (1998).
Ross, Jeffrey S. et al., "The and HER-2/neu oncogene: prognostic factor, predictive factor and target for therapy", Seminars in Cancer Biology, vol. 9, pp. 125-138, (1999).
Sadasivan et al., "Overexpression of Her-2/Neu May Be an Indicator of Poor Prognosis in Prostate Cancer", J. Urol. 150:126-131 (Jul. 1993).
Sarup et al., "Characterization of an Anti-P185Aaa.d Monoclonal Antibody that Stimulates Receptor Function and Inhibits Tumor Cell Growth" Growth Regulation 1: 72-82, (1991).
Schaefer et al., "A Discrete Three-amino Acid Segment (LVT) at the C-terminal End of Kinase-impaired ErbB3 is required for Transactivation of ErbB2" Journal of Biological Chemistry 274(2):859-866, (1999).
Schaefer et al., "y-Heregulin: A Novel Heregulin Isoform That is an Autocrine Growth Factor for the Human Breast Cancer Cell Line, MDA-M5-175" Oncogene 15: 1385-1394, (1997).
Scher et al., "Changing Pattern of Expression of the Epidermal Growth Factor Receptor and Transforming Growth Factor a in the Progression of Prostatic Neoplasms" Clinical Cancer Research 1: 545-550, (May 1995).
Schlom, "Monoclonal Antibodies: They're More and Less Than You Think" Molecular Foundations of Oncology, Broder, S. ed., Baltimore, MD: Williams & Wilkins, chapter 6, pp. 95-134 (1991).
Scott et al., "p185aEaa Signal Transduction in Breast Cancer Cells" Journal of Biological Chemistry 266(22): 14300-14305 (Aug. 5, 1991).

Seifert et al., "Dexrazoxane in the prevention of doxorubicin-induced cardiotoxicity", Annals of Pharmacotherapy 28(9): 1063-1072 (Sep. 1994).
Shawver et al., "Ligand-Like Effects Induced by Anti-c-erbB-2 Antibodies Do Not Correlate Not Required for Growth Inhibition of Human Carcinoma Cells", Cancer Research 54(5): 1367-1373, (1994).
Sheng et al , "Inhibition of Human Colon Cancer Cell Growth by gaective Inhibition of Cyclooxygenase-2", J. Clin. Invest. 99(9): 2254-2259, (May 1997).
Shepard et al., "Monoclonal Antibody Therapy of Human Cancer: Taking the BER2 Protooncogene to the Clinic" J. Clin. Immunel 11(3): 117-127 (1991).
Singal and Iliskovic, "Doxorubicin-induced cardiomyopathy" New England J. of Medicine 339(13): 900-905, (Sep. 24, 1998).
Singel et al., Combination therapy with probucol prevents adriamycin-induced cardicmyopathy Journal of Molecular & Cellular Cardiology 27(4): 1055-1063, (Apr. 1995).
Skrepnik et al., "Recombinant Oncotoxin AR209 (anti-p185ernb[-2]) Diminishes Human Prostate Carcinoma Xenografts" Journal of Urology 161: 984-989 (1999).
Slamon et al., "Human Breast Cancer: Correlation of Relapse and Survival with Amplification of the HER-2/neu Oncogene" Science 235:177-182 (Jan. 9, 1987).
Slamon et al., "Studies of the HER-2/neu Proto-Oncogene in Human Breast and Ovarian Cancer" Science 244: 707-712, (May 12, 1989).
Slamon et al., "Use of chemotherapy plus a monoclonal antibody against HER2 for metastatic breast cancer that overexpresses BER2" New England J. of Medicine 344(11): 783-792, (2001).
Sliwkowski at al., "A humanized monoclonal antibody for the treatment of HER2 overexpressing breast cancer" Proceedings of the American Association for Cancer Research (abstract only) 37: 625-626, (Mar. 1996).
Sliwkowski et al., "Coexpression of erbB2 and erbB3 Proteins Reconstitutes a High Affinity Receptor for Heregulin" Journal of Biological Chemistry 269(20): 14661-14665, (1994).
Stancovski at al., "Mechanistic Aspects of the Opposing Effects of Monoclonal Antibodies to the ERBB2 Receptor on Tumor Growth" Proc. Natl. Acad. Sol. DSA 88(19): 8691-8695, (1991).
Statement Regarding HERCEPTIN Clinical Trials pp. 1 (2004).
Stern and Kamps., "EGF-Stimulated Tyrosine Phosphorylation of p185nen: A Potential Model for Receptor Interactions." EMBO Journal 7(4): 995-1001 (1988).
Strobel and Cannistra, "pl-integrins partly mediate binding of ovarian cancer cells to peritoneal mesothelium in vitro" Gynecologic Oncology 73(3} : 362-367 (Jun. 1999).
Tagliabue at al., "Selection of Monoclonal Antibodies Which Induce Internalization and Phosphorylation of p185nER[2] and Growth Inhibition of Cells With HER2/NEU Gene Amplification", International Journal of Cancer 47(6): 933-937 (Apr. 1, 1991).
Tendon et al., "HER-2/neu oncogene protein and prognosis in breast cancer" Journal of Clinical Oncology 7(8): 1120-11213, (Aug. 1989).
Tetu, Bernard et al., "Prevalence and Clinical Significance of HER-2/neu, p53 and Rb Expression in Primary Superficial Bladder Cancer", The Journal of Urology, vol. 155, 1784-1788, (1996).
Thatcher et al., "Gefitinib plus best supportive care in previously treated patients with refractory advanced non-small-cell lung cancer: results from a randomised, placebo-controlled, multicentre study (Iressa Survival Evaluation in Lung Cancer)" Lancet 366(9496): 1527-1537 (Oct. 29, 2005).
Tockman at al., "Considerations in Bringing a Cancer Biomarker to Clinical Application", Cancer Research 52:2711s-2718s (May 1, 1992).
Tokumo et al., "Double mutation an• gene copy number of EGFR in gefitinib refractory non-small-cell lung cancer" Lung Cancer 53: 117-121 (2006).
Tripp et al., "Relationship between EGFR overexpression and gene amplification status in central nervous system gliomas" Analytical & Quantitative Cytology & Histology 27(2):71-78 (Apr. 2005).
Tsao et al., "Erlotinib in lung cancer—molecular and clinical predictors of outcome", New England J. of Medicine 353(2): 133-144, (Jul. 14, 2005).

Vadlamudi et al., "Regulation of Cyclooxygenase-2 pathway by HER2 receptor" Oncogene, 18: 305-314, (1999).

Van de Vijver et al., "Neu-Protein Overexpression in Breast Cancer: Association With Comedo-Type Ductal Carcinoma In Situ and Limited Prognostic Value in Stage II Breast Cancer." New England J. of Medicine 319(19): 1239-1245 (Nov. 10, 1988).

Van Lom et al., "In Situ Hybridization on May-Grunwald Giemsa-Stained Bone Marrow and Blood Smears of Patients With Hematologic Disorders Allows Detection of Cell-Lineage-Specific Cytogenetic Abnormalities" Blood 82(3): 884-888, (Aug. 1, 1993).

Vitetta and Uhr, "Monoclonal Antibodies as Agonists: An Expanded Role for Their Use in Cancer Therapy", Cancer Research 54(20): 5301-5309, (Oct. 15, 1994).

Wada et al., "Intermolecular Association of the p185neu Protein and EGF Receptor Modulates EGF Receptor Function" Cell 61: 1339-1347 (Jun. 29, 1990).

Waha et al., "A polymerase chain reaction-based assay for the rapid detection of gene amplification in human tumors" Diagnostic Molecular Pathology 5(2):147-150 (Jun. 1996).

Walker et al., "An Evaluation of Immunoreactivity for c-erbB-2 Protein as a Marker of Poor Short-Term Prognosis in Breast Cancer." British Journal of Cancer 60(3): 426-429, (1989).

Wang et al., "Epidermal growth factor receptor protein expression and gene amplification in small cell carcinoma of the urinary bladder", Clinical Cancer Research 13(3): 953-957, (2007).

Wang et al., "Laboratory Assessment of the Status of Her-2/neu Protein and oncogene in Breast Cancer Specimens: Comparison of Immunohistochemistry Assay with Fluorescence in Situ Hybridisation Assays." J. Clinical Pathology 53(5): 374-381 (May 2000).

Weiner et al., "Expression of the neu Gene-encoded Protein (P185nen) in Human Non-Small Cell Carcinomas of the Lung" Cancer Research 50(2): 421-425 (Jan. 15, 1990).

Werther et al., "Humanization of an Anti-Lymphocyte Function-Associated Antigen (LPA)-1 Monoclonal Antibody and Reengineering of the Humanized Antibody for Binding to Rhesus LFA-1" J. of Immunology 157: 4986-4995 (1996).

Williams et al., "Expression of c-erbB-2 in Human Pancreatic Adenocarcinomas" Pathobiology 59(1): 46-52 (1991).

Winstanley et al., "The long term prognostic significance of c-erbB-2 in primary breast cancer" British Journal of Cancer 63(3): 447-450 (Mar. 1991).

Winter, "Antibody-based Therapy—Humanized Antibodies" TIPS, UK:Elsevier Science Publishers vol. 14: 139-143, (1993).

Wofsy et al., "Modification and Use of Antibodies to Label Cell Surface Antigens" Selected Methods in Cellular Immunology, Mishel and Schligi, eds., San Francisco:WJ Freeman Co., Chapter 13, pp. 287-304 (1980).

Wolff et al., "American society of clinical-oncology/college of American pathologists guideline recommendations for human epidermal growth factor receptor 2 testing in breast cancer", Arch Pathol Lab Med 131: 18-43 (Jan. 2007).

Wolman et al., "An Approach to Definition. of Genetic Alterations in Prostate Cancer", Diagnostic Molecular Pathology 1(3):192-199 (Sep. 1992).

Worthylake et al., "Structural Aspects of the Epidermal Growth Factor Receptor Required for Transmodulation of erbB-2/neu" Journal of Biological Chemistry 272(13): 8594-8601, (Mar. 28, 1997).

Wright et al., "An Incomplete Program of Cellular. Tyrosine Phosphorylations Induced by Kinase-defective Epidermal Growth Factor Receptors" Journal of Biological Chemistry 270(20):12085-12093, (1995).

Wright et al., "Expression of c-erbB-2 Oncoprotein: A Prognostic Indicator in Human Breast Cancer", Cancer Research 49(8): 2087-2090, (Apr. 15, 1989).

Wu et al., "Antibody-Induced Growth Inhibition is Mediated Through Immunochemically and Functionally Distinct Epitopes on the Extracellular Domain of the c-erbB-2 (HER-2/neu) Gene Product p185" International Journal of Cancer 53(3):401-408 (Feb. 1, 1993).

Wu et al., "Apoptosis Induced by an Anti-Epidermal Growth Factor Receptor Monoclonal Antibody in a Human Colorectal Carcinoma Cell Line and Its Delay by Insulin" Journal of Clinical Investigation 95(4): 1897-1905, (Apr. 1995).

Yeh at al., "From HER2/Neu signal cascade to androgen receptor and its coactivators: A novel pathway by induction of androgen target genes through MAP kinase in prostate cancer cells" Proc. Natl. Acad. Sci. USA 96: 5458-5463, (May 1999).

Yokota at al., "Amplification of c-erbB-2 Oncogene in Human Adenocarcinomas in Vivo" Lancet 1(8484): 765-767 (Apr. 5, 1986).

Yonemura et al., "Evaluation of Immunoreactivity for erbB-2 Protein as a Marker of Poor Short Term Prognosis in Gastric Cancer" Cancer Research 51(3): 1034-1038, (1991).

Zhang et al., "Neuregulin-3 (NRG3): A novel neural tissue-enriched protein that binds activates ErbB4" Proc. Natl. Acad. Sci. USA 94: 9562-9567 (Sep. 22, 1997).

Zhang et al., "Shared antigenic epitopes and pathobiological functions of anti-p186nerineu monoclonal antibodies" Experimental and Molecular Pathology 67: 15-25 (1999).

Zhau et al., "Amplification and Expression of the c-erb B-2/neu Proto-Oncogene in Human Bladder Cancer", Molecular Carcinogenesis 3(5): 254-257 (1990).

Zitzelsberger at al., "Numerical Abnormalities of Chromosome 7 in Human Prostate Cancer Detected by Fluorescence in Situ Hybridization (FISH) on Paraffin-Embedded Tissue Sections With Centromere-Specific DNA Probes" Journal of Pathology 172(4): 325-335 (Apr. 1994).

Ohnishi, et al., "Prolonged survival of mice with human gastric cancer treated with an anti-c-ErbB-2 monoclonal antibody", British Journal of Cancer, vol. 71, No. 5, pp. 969-973, (1995).

Sauter, et al., "Guidelines for human epidermal growth factor receptor 2 testing: Biological and methodologic considerations", Journal of Clinical Oncology, 27: 1-11, (2009).

Summons to attend oral proceedings regarding Oppositions to EP 1210115 dated Sep. 21, 2011.

Sauter, et al., "Reply to E.H. Hammond", Journal of Clinical Oncology, 27930): e155-e157, (2009).

Mass, et al Abstract 291, ASCO 36$^{th}$ meeting, May 20-23, 2000 and opening page of abstract book.

Pegram, et al., "HER-2/neu as a predictive marker of response to breast cancer therapy", Breast Cancer Research and Treatment, 52: 65-77, (1998).

Ross, et al., "HER-2/neu gene amplification determined by fluorescence in-situ hybridization (FISH) is superior to immunohistochemistry (IHC) for risk-group assessment in node-negative breast cancer", Abstracts—poster session III 277, (1998).

Harbeck, et al., "HER-2/neu gene amplification by fluorescence in-situ hybridization allows risk-group assessment in node-negative breast cancer", International Journal of Oncology, 14: 663-671, (1999).

Ross, et al., "HER-2/neu (c-erb-B2) gene and protein in breast cancer", Am. J. Clin. Pathol., 114(Suppl.1): S53-S67, (1999).

Press, et al., "HER-2 gene amplification, HER-2 and epidermal growth factor receptor mRNA and protein expression, and Lapatinib efficacy in women with metastatic breast cancer", Cancer Therapy: clinical, 14(23): 7861-7870, (2008).

Herceptin revised US label 2002.

Herceptin revised US label 2010.

Her2-Diagnostik—Ein Leitfaden fur Brustkrebs-Patientinnen.

FDA/CBER Clinical Review Briefing document dated Nov. 5, 2001.

Sequence of webpages archived by the Wayback machine from the website of the ASCO conference in 2000. Apr. 26, 2012.

The webpage archived by the Wayback machine from the website of the ASCO conference in 2000 that adresses the availability of the Annual Meeting Abstracts at the conference. Apr. 26, 2012.

\* cited by examiner

GENE DETECTION ASSAY FOR IMPROVING THE LIKELIHOOD OF AN EFFECTIVE RESPONSE TO A HER2 ANTIBODY CANCER THERAPY

CROSS-REFERENCE TO RELATED APPLICATIONS

This application is a continuation of U.S. patent application Ser. No. 11/690,304, filed Mar. 23, 2007 now U.S. Pat. No. 8,076,066, which is a continuation application of and claims priority to U.S. patent application Ser. No. 09/863,101 filed May 18, 2001 (abandoned) which claims priority under 35 U.S.C. §119(e) of provisional application 60/205,754, filed May 19, 2000, all of which are incorporated herein by reference in their entireties.

FIELD OF THE INVENTION

The present invention concerns the treatment of cancers characterized by the overexpression of a tumor antigen, such as an ErbB receptor, particularly HER2. More specifically, the invention concerns more effective treatment of human patients susceptible to or diagnosed with cancer, in which the tumor cells overexpress ErbB as determined by a gene amplification assay, with an ErbB antagonist, e.g., an anti-ErbB antibody. The invention further provides pharmaceutical packages for such treatment.

BACKGROUND OF THE INVENTION

Advancements in the understanding of genetics and developments in technology and epidemiology have allowed for the correlation of genetic abnormalities with certain malignancies as well as risk assessment of an individual for developing certain malignancies. However, most of the methodologies available for evaluation of tissue for the presence of genes associated with or predisposing an individual to a malignancy have well-known drawbacks. For example, methods that require disaggregation of the tissue, such as Southern, Northern, or Western blot analysis, are rendered less accurate by dilution of the malignant cells by the normal or otherwise non-malignant cells that are present in the same tissue. Furthermore, the resulting loss of tissue architecture precludes the ability to correlate malignant cells with the presence of genetic abnormalities in a context that allows morphological specificity. This issue is particularly problematic in tissue types known to be heterogeneous, such as in human breast carcinoma, where a significant percentage of the cells present in any area may be non-malignant.

The her2/neu gene encodes a protein product, often identified as p185HER2. The native p185HER2 protein is a membrane receptor-like molecule with homology to the epidermal growth factor receptor (EGFR). Amplification and overexpression of HER2 in human breast cancer has been correlated with shorter disease-free interval and shorter overall survival in some studies (van de Vijver et al. New Eng. J. Med. 317:1239 (1988); Walker et al. Br. J. Cancer 60:426 (1989); Tandon et al. J. Clin. Invest. 7:1120 (1989); Wright et al. Cancer Res. 49:2087 (1989); McCann et al. Cancer Res 51:3296 (1991); Paterson et al. Cancer Res. 51:556 (1991); and Winstanley et al. Br. J. Cancer 63:447 (1991)) but not in others (Zhou et al. Oncogene 4:105 (1989); Heintz et al. Arch Path Lab Med 114:160 (1990); Kury et al. Eur. J. Cancer 26:946 (1990); Clark et al. Cancer Res. 51:944 (1991); and Ravdin et al. J. Clin. Oncol. 12:467-74 (1994)).

In an initial evaluation of 103 patients with breast cancer, those having more than three tumor cell positive axillary lymph nodes (node positive) were more likely to overexpress HER2 protein than patients with less than three positive nodes (Slamon et al. Science 235:177 (1987)). In a subsequent evaluation of 86 node-positive patients with breast cancer, there was a significant correlation among the extent of gene amplification, early relapse, and short survival. HER2 overexpression was determined using Southern and Northern blotting, which correlate with the HER2 oncoprotein expression evaluated by Western blotting and immunohistochemistry (IHC) (Slamon et al. Science 235:177 (1987); Slamon et al. Science 244:707 (1989)). The median period of survival was found to be approximately 5-fold shorter in patients with more than five copies of the her2 gene than in patients without gene amplification. This correlation was present even after correcting for nodal status and other prognostic factors in multivariate analyses. These studies were extended in 187 node-positive patients and indicated that gene amplification, increased amounts of mRNA (determined by Northern blotting), and increased protein expression (determined immunohistochemically) were also correlated with shortened survival time (Slamon et al. Science 244:707 (1989)); (see also U.S. Pat. No. 4,968,603). Nelson et al. have compared her2/neu gene amplification using FISH with immunohistochemically determined overexpression in breast cancer (Nelson et al. Modern Pathology 9 (1) 21A (1996)).

Immunohistochemical staining of tissue sections has been shown to be a reliable method of assessing alteration of proteins in a heterogeneous tissue. Immunohistochemistry (IHC) techniques utilize an antibody to probe and visualize cellular antigens in situ, generally by chromagenic or fluorescent methods. This technique excels because it avoids the unwanted effects of disaggregation and allows for evaluation of individual cells in the context of morphology. In addition, the target protein is not altered by the freezing process.

However, in the clinical trial assay (CTA), IHC of formaldehyde-fixed, paraffin embedded tissue samples only demonstrated 50%-80% sensitivity, relative to frozen IHC samples (Press, Cancer Research 54:2771 (1994)). Thus, IHC can lead to false negative results, excluding from treatment patients who might benefit from the treatment.

Fluorescence in situ hybridization (FISH) is a recently developed method for directly assessing the presence of genes in intact cells. FISH is an attractive means of evaluating paraffin-embedded tissue for the presence of malignancy because it provides for cell specificity, yet overcomes the cross-linking problems and other protein-altering effects caused by formalin fixation. FISH has historically been combined with classical staining methodologies in an attempt to correlate genetic abnormalities with cellular morphology (see, e.g., Anastasi et al., Blood 77:2456-2462 (1991); Anastasi et al., Blood 79:1796-1801 (1992); Anastasi et al., Blood 81:1580-1585 (1993); van Lom et al., Blood 82:884-888 (1992); Wolman et al., Diagnostic Molecular Pathology 1(3): 192-199 (1992); Zitzelberger, Journal of Pathology 172:325-335 (1994)).

To date, there has been no correlation of her2 gene amplification with anti-HER2 antibody treatment outcome, only with disease prognosis. The standard assay has been IHC on formalin fixed, paraffin embedded samples. These samples, when scored as 3+ or 2+, identify patients who are likely to benefit from treatment with an anti-HER2 antibody, like HERCEPTIN®. The 3+ and 2+ scores correlate with her2 gene amplification, e.g., as tested by FISH. However, there remains a need for more effective identification of candidates for successful ErbB antagonist therapies, such as HERCEPTIN® treatment.

SUMMARY OF THE INVENTION

The invention advantageously provides a method for increasing likelihood of effectiveness of an ErbB antagonist cancer treatment. The method comprises administering a cancer treating dose of the ErbB antagonist to a subject wherein an erbB gene in tumor cells in a tissue sample from the subject has been found to be amplified. Preferably the ErbB is HER2. In a specific embodiment, the method further comprises administering a cancer treating dose of a chemotherapeutic, particularly a taxol.

In a specific preferred embodiment, exemplified herein, the invention provides a method for increasing likelihood of effectiveness of an anti-HER2 antibody to treat cancer. This method comprises administering a cancer treating dose of the anti-HER2 antibody to the subject in whom a her2 gene in tumor cells in a tissue sample from the subject have been found to be amplified.

The unexpected clinical results underlying the invention, in which gene amplification proved to be a more effective indication of antibody-based tumor therapy than protein detection by immunohistochemistry, extends to tumor antigens in general. Thus, any anti-tumor-specific antigen based antibody therapy can have increased likelihood of success in patients who are found to have gene amplification of the gene encoding the tumor antigen.

A particular advantage of the invention is that it permits selection of patients for treatment who, based on immunohistochemical criteria, would be excluded. Thus, in a specific embodiment, the subject has been found to have an antigen level corresponding to a 0 or 1+ score for HER2 by immunohistochemistry on a formaldehyde-fixed tissue sample.

The invention further provides a pharmaceutical package comprising an ErbB antagonist for treating a cancer, and instructions to administer the ErbB antagonist to a subject if an erbB gene in tumor cells in a tissue sample from the subject is amplified. Preferably the ErbB antagonist is an anti-ErbB antibody, such as an anti-HER2 antibody. In a further aspect, the instructions also teach administering a cancer treating dose of a chemotherapeutic, e.g., a taxol. Such pharmaceutical packages, including the instructions for use, can be provided for any antibody-based therapeutic specific for a tumor-specific antigen.

DETAILED DESCRIPTION

The present invention advantageously permits treatment of patients who have a greater likelihood of responding to the treatment by administering therapeutic agents, i.e., anti-tumor antigen therapeutic antibodies or ErbB receptor antagonists, to patients who are found to have an amplified gene encoding such a tumor antigen or ErbB receptor protein. The invention is based, in part, on the unexpected discovery that her2 gene amplification, e.g., as detected by fluorescence in situ hybridization (FISH), although it correlates with HER2 expression as detected by immunohistochemistry (NC), provides a more accurate basis for selecting patients for treatment because FISH status unexpectedly correlates better with response to treatment. This outcome was surprising in part because FISH status has about the same rate of correlation with a clinical trial assay (CTA) NC assay as another NC assay (HERCEPTEST®). Based on this observation, FISH would be expected to have a similar correlation with treatment response. This outcome also surprises because direct measurement of protein (by immunoassay) would be expected to provide a more accurate assessment of a cancer therapy targeted to the protein than an indirect measure of expression, like gene amplification.

Evaluation of patient groups and subgroups demonstrates the power of gene amplification analysis for selecting patients more likely to respond to treatment. NC provides a score for HER2 expression on tumor cells: 0 (no expression) through 3+ (very high levels of expression). Clinical selection criteria exclude patients with 0 and 1+ scores and select patients with 2+ and 3+ scores. The data show that 14% of combined 2+/3+ patients respond to HERCEPTIN®, while 20% of FISH+ (amplified her2 gene) patients respond to HERCEPTIN®. The 3+ subgroup has a 17% response rate, which is very close to the FISH+ subjects' response rate. However, the 2+ subgroup has less than half the response rate of FISH+ subjects. Thus, gene amplification clearly differentiates large subpopulations within the 2+ subgroup, permitting more effective treatment for those who are FISH+, and quickly identifying patients for whom alternative treatment modalities are appropriate and should commence immediately.

Gene amplification analysis also identifies patients who are unnecessarily excluded because of anomalies in the IHC analysis, particularly when the tests are performed on formalyn fixed, paraffin embedded samples (such sample processing can disrupt or destroy antibody epitopes on the HER2 protein, but has much less impact on gene amplification assays). As shown in the examples, a subset of 0 and 1+ subjects are FISH+. These patients are likely to respond to anti-HER2 antibody therapy, e.g., with HERCEPTIN®, although by IHC criteria they would be excluded from receiving this treatment.

Thus, the present invention advantageously permits inclusion of patients who are more likely to benefit from treatment but who, by standard IHC criteria, would be excluded from treatment. At the same time, the invention permits exclusion of patients who should promptly seek an alternative mode of treatment because the anti-tumor antigen therapy (i.e., ErbB antagonist or tumor antigen-specific therapeutic antibody) is not likely to succeed.

In short, the present invention is a powerful adjunct to INC assays for target protein expression level-based selection of patients. It can also be employed on its own, i.e., without IHC, to provide initial screening and selection of patients. The invention significantly improves screening and selection for subjects to receive a cancer-treating dose of an anti-tumor antigen therapeutic antibody treatment, ErbB receptor antagonist treatment, and other treatment targeted to overexpressed tumor antigens (or tumor-specific antigens), resulting in an increased likelihood of benefit from such treatments.

In another aspect, the invention concerns an article of manufacture or package, comprising a container, a composition within the container comprising an ErbB antagonist, e.g., an anti-ErbB antibody (or other anti-tumor-specific antigen antibody), optionally a label on or associated with the container that indicates that the composition can be used for treating a condition characterized by overexpression of ErbB receptor, and a package insert containing instructions to administer the antagonist to patients who have been found to have an amplified erbB gene.

DEFINITIONS

As used herein, an "ErbB receptor" is a receptor protein tyrosine kinase which belongs to the ErbB receptor family and includes EGFR, HER2, ErbB3, and ErbB4 receptors, as well as TEGFR (U.S. Pat. No. 5,708,156) and other members of this family to be identified in the future. The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a native sequence ErbB receptor or an amino acid sequence variant thereof. Preferably the ErbB receptor is native sequence human ErbB receptor.

ErbB receptors are examples of tumor-specific antigens or tumor antigens. The term "tumor antigen" is used herein to refer to a protein that is expressed at a higher level on tumor cells compared to normal cells. Generally, the normal cells for comparison are of the same tissue type, particularly phenotype, as the tumor, or from which the tumor arose. A "tumor specific antigen" refers to an antigen expressed either preferentially or only on tumor cells. Examples of tumor-specific antigens include, in addition to the ErbB receptors, MART1/Melan A, gp-100, and tyrosinase (in melanoma); MAGE-1 and MAGE-3 (in bladder, head and neck, and non-small cell carcinoma); HPV EG and E7 proteins (in cervical cancer); Mucin/MUC-1 (in breast, pancreas, colon, and prostate cancers); prostate specific antigen PSA (in prostate cancer); and caminoembryonic antigen/CEA (in colon, breast, and gastrointestinal cancers).

By "amplification" is meant the presence of one or more extra gene copies of erbB or other tumor antigen-encoding gene in a chromosome complement. Gene amplification can result in overexpression of protein, e.g., ErbB receptor protein. Gene amplification in cells from a tissue sample can be measured by many techniques, particularly Fluorescence in situ Hybridization (FISH), but also including and not limited to quantitative PCR, quantitative Southern hybridization, and the like.

By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like. In one embodiment of the invention, the tissue sample is "non-hematologic tissue" (i.e., not blood or bone marrow tissue).

For the purposes herein a "section" of a tissue sample is meant a single part or piece of a tissue sample, e.g., a thin slice of tissue or cells cut from a tissue sample. It is understood that multiple sections of tissue samples may be taken and subjected to analysis according to the present invention, provided that it is understood that the present invention comprises a method whereby the same section of tissue sample may be analyzed at both morphological and molecular levels, or may be analyzed with respect to both protein and nucleic acid.

By "correlate" or "correlating" is meant comparing, in any way, the performance and/or results of a first analysis with the performance and/or results of a second analysis. For example, one may use the results of a first analysis in carrying out the second analysis and/or one may use the results of a first analysis to determine whether a second analysis should be performed and/or one may compare the results of a first analysis with the results of a second analysis. In relation to IHC combined with FISH, one may use the results of INC to determine whether FISH should be performed and/or one may compare the level of protein expression with gene amplification to further characterize a tumor biopsy (e.g. to compare HER2 protein expression with her2 gene amplification). One advantageous feature of the invention is the ability to identify patients likely to benefit from treatment using FISH even if IHC indicates that they are antigen low.

By "nucleic acid" is meant to include any DNA or RNA, for example, chromosomal, mitochondrial, viral and/or bacterial nucleic acid present in tissue sample. The term "nucleic acid" encompasses either or both strands of a double stranded nucleic acid molecule and includes any fragment or portion of an intact nucleic acid molecule.

By "gene" is meant any nucleic acid sequence or portion thereof with a functional role in encoding or transcribing an RNA (rRNA, tRNA, or mRNA, the latter capable of translation as a protein) or regulating other gene expression. The gene may consist of all the nucleic acids responsible for encoding a functional protein or only a portion of the nucleic acids responsible for encoding or expressing a protein. The nucleic acid sequence may contain a genetic abnormality within exons, introns, initiation or termination regions, promoter sequences, other regulatory sequences or unique adjacent regions to the gene.

By "ErbB ligand" is meant a polypeptide which binds to and/or activates an ErbB receptor. The ErbB ligand of particular interest herein is a native sequence human ErbB ligand such as Epidermal Growth Factor (EGF) (Savage et al., J. Biol. Chem. 247:7612-7621 (1972)); Tansforming Growth Factor alpha (TGF-alpha) (Marquardt et al., Science 223: 1079-1082 (1984)); amphiregulin, also known as schwanoma or keratinocyte autocrine growth factor (Shoyab et al. Science 243:1074-1076 (1989); Kimura et al. Nature 348:257-260 (1990); and Cook et al. Mol. Cell. Biol. 11:2547-2557 (1991)); betacellulin (Shing et al., Science 259:1604-1607 (1993); and Sasada et al. Biochem. Biophys. Res. Commun. 190:1173 (1993)); heparin-binding epidermal growth factor (HB-EGF) (Higashiyama et al., Science 251:936-939 (1991)); epiregulin (Toyoda et al., J. Biol. Chem. 270:7495-7500 (1995); and Komurasaki et al. Oncogene 15:2841-2848 (1997)), a heregulin (see below); neuregulin-2 (NRG-2) (Carraway et al., Nature 387:512-516 (1997)); neuregulin-3 (NRG-3) (Zhang et al., Proc. Natl. Acad. Sci. 94:9562-9567 (1997)); or cripto (CR-1) (Kannan et al., J. Biol. Chem. 272 (6):3330-3335 (1997)). ErbB ligands that bind EGFR include EGF, TGF-alpha, amphiregulin, betacellulin, HB-EGF andepiregulin. ErbB ligands which bind HER3 include heregulins. ErbB ligands capable of binding HER4 include betacellulin, epiregulin, HB-EGF, NRG-2, NRG-3 and heregulins.

"Heregulin" (HRG) when used herein refers to a polypeptide comprising an amino acid sequence encoded by the heregulin gene product as disclosed in U.S. Pat. No. 5,641, 869 or Marchionni et al., Nature, 362:312-318 (1993), and biologically active variants of such polypeptides. Examples of heregulins include heregulin-alpha, heregulin-beta1, heregulin-beta2, and heregulin-beta3 (Holmes et al., Science, 256:1205-1210 (1992); and U.S. Pat. No. 5,641,869); neu differentiation factor (NDF) (Peles et al. Cell 69: 205-216 (1992)); acetylcholine receptor-inducing activity (ARIA) (Falls et al. Ce1172:801-815 (1993)); glial growth factors (GGFs) (Marchionni et al., Nature, 362:312-318 (1993)); sensory and motor neuron derived factor (SMDF) (Ho et al. J. Biol. Chem. 270:14523-14532 (1995)); gamma-heregulin (Schaefer et al. Oncogene 15:1385-1394 (1997)). An example of a biologically active fragment/amino acid sequence variant of a native sequence HRG polypeptide, is an EGF-like domain fragment (e.g., HRG-beta1, 177-244).

An "ErbB hetero-oligomer" herein is a noncovalently associated oligomer comprising at least two different ErbB receptors. Such complexes may form when a cell expressing two or more ErbB receptors is exposed to an ErbB ligand and can be isolated by immunoprecipitation and analyzed by SDS-PAGE as described in Sliwkowski et al., (J. Biol. Chem., 269(20):14661-14665 (1994)), for example. Examples of such ErbB hetero-oligomers include EGFR-HER2, HER2-HER3, and HER3-HER4 complexes. Moreover, the ErbB hetero-oligomer may comprise two or more HER2 receptors combined with a different ErbB receptor, such as HER3, HER4, or EGFR. Other proteins, such as a cytokine receptor subunit (e.g., gp130), may be included in the hetero-oligomer.

The terms "ErbB1", "epidermal growth factor receptor" and "EGFR" are used interchangeably herein and refer to native sequence EGFR as disclosed, for example, in Carpenter et al. (Ann. Rev. Biochem. 56:881-914 (1987)), including variants thereof (e.g., a deletion mutant EGFR as in Humphrey et al., (Proc. Natl. Acad. Sci. USA 87:4207-4211 (1990)). ErbB1 refers to the gene encoding the EGFR protein product. Examples of antibodies which bind to EGFR include MAb 579 (ATCC CRL HB 8506), Mab 455 (ATCC CRL HB 8507), MAb 225 (ATCC CRL 8508), MAb 528 (ATCC CRL 8509) (see, U.S. Pat. No. 4,943,533) and variants thereof, such as chimerized 225 (C225) and reshaped human 225 (H225) (see, PCT Publication No. WO 96/40210).

The expressions "ErbB2" and "HER2" are used interchangeably herein and refer to native sequence human HER2 protein described, for example, in Semba et al., (Proc. Natl. Acad. Sci. USA 82:6497-6501 (1985)) and Yamamoto et al. (Nature 319:230-234 (1986)) (Genebank accession number X03363), and variants thereof. The term erbB2 refers to the gene encoding human HER2 and neu refers to the gene encoding rat p185neu. Preferred HER2 is native sequence human HER2. Examples of antibodies which bind HER2 include MAbs 4D5 (ATCC CRL 10463), 2C4 (ATCC HB-12697), 7F3 (ATCC HB-12216), and 7C2 (ATCC HB-12215) (see, U.S. Pat. No. 5,772,997; PCT Publication No. WO 98/17797; and U.S. Pat. No. 5,840,525, expressly incorporated herein by reference). Humanized anti-HER2 antibodies include huMAb4D5-1, huMAb4D5-2, huMAb4D5-3, huMAb4D5-4, huMAb4D5-5, huMAb4D5-6, huMAb4D5-7, and huMAb4D5-8 (HERCEPTIN®) as described in Table 3 of U.S. Pat. No. 5,821,337, which is expressly incorporated herein by reference; and humanized 520C9 (PCT Publication No. WO 93/21319). Human anti-HER2 antibodies are described in U.S. Pat. No. 5,772,997 and PCT Publication No. WO 97/00271.

"ErbB3" and "HER3" refer to the receptor polypeptide as disclosed, for example, in U.S. Pat. Nos. 5,183,884 and 5,480,968, as well as Kraus et al. (Proc. Natl. Acad. Sci. USA) 86:9193-9197 (1989)), including variants thereof. Exemplary antibodies that bind HER3 are described in U.S. Pat. No. 5,968,511, e.g., the 8B8 antibody (ATCC BIB-12070) or a humanized variant thereof. The terms "ErbB4" and "HER4" herein refer to the receptor polypeptide as disclosed, for example, in European Application No. EP 599,274; Plowman et al., (Proc. Natl. Acad. Sci. USA, 90:1746-1750 (1993)); and Plowman et al., (Nature, 366:473-475 (1993)), including variants thereof such as the HER4 isoforms disclosed in PCT Publication No. WO 99/19488.

An "ErbB antagonist" is any molecule that binds to an ErbB receptor and blocks ligand activation of the ErbB receptor. Such antagonists include, but are not limited to, modified ligands, ligand peptides (i.e., ligand fragments), soluble ErbB receptors, and, preferably, anti-ErbB antibodies.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the ErbB antagonist, e.g., anti-ErbB2 antibody, and more generally, any cancer in which administration of an antibody against an over-expressed antigen can treat the cancer. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" is used to refer to an amount having antiproliferative effect. Preferably, the therapeutically effective amount elicits antibody-mediated cytotoxicity, activates complement, has apoptotic activity, or is capable of inducing cell death, and preferably death of benign or malignant tumor cells, in particular cancer cells. Efficacy can be measured in conventional ways, depending on the condition to be treated. For cancer therapy, efficacy can, for example, be measured by assessing the time for disease progression (TTP), survival, tumor size, or determining the response rates (RR) (see the Example below).

The terms "cancer" and "cancerous" refer to or describe the physiological condition in mammals that is typically characterized by unregulated cell growth. Examples of cancer include but are not limited to, carcinoma, lymphoma, blastoma, sarcoma, melanoma, and leukemia. More particular examples of such cancers include squamous cell cancer, small-cell lung cancer, non-small-cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma, and various types of head and neck cancer.

An "ErbB-expressing cancer" is one comprising cells which have ErbB protein present at their cell surface, such that an anti-ErbB antibody is able to bind to the cancer.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$, and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carzinophilin, chromomycins, dactinomycin, daunorubicin, 6-diazo-5-oxo-L-norleucine, doxorubicin, epirubicin, mitomycins, mycophenolic acid, nogalamycin, olivomycins, peplomycin, potfiromycin, puromycin, streptonigrin, streptozocin, tubercidin, ubenimex, zinostatin, zorubicin; antimetabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK®; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL®, Bristol-Myers Squibb Oncology, Princeton, N.J.) and doxetaxel (Taxotere, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; caminomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone; and anti-androgens such as flutamide and nilutamide; and pharmaceutically acceptable salts, acids or derivatives of any of the above.

A "growth inhibitory agent" when used herein refers to a compound or composition which inhibits growth of a cell, especially an ErbB-overexpressing cancer cell either in vitro or in vivo. Thus, the growth inhibitory agent is one which significantly reduces the percentage of ErbB overexpressing cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The 4D5 antibody (and functional equivalents thereof) can also be employed for this purpose.

ErbB Receptor Tyrosine Kinases

The ErbB receptor tyrosine kinases are important mediators of cell growth, differentiation and survival. The receptor family includes at least four distinct members including Epidermal Growth Factor Receptor (EGFR or ErbB1), HER2 (ErbB2 or p185neu), HER3 (ErbB3), and HER4 (ErbB4 or tyro2).

EGFR, encoded by the ErbB1 gene, has been causally implicated in human malignancy. In particular, increased expression of EGFR has been observed in breast, bladder, lung, head, neck and stomach cancer, as well as glioblastomas. Increased EGFR receptor expression is often associated with increased production of the EGFR ligand, Transforming Growth Factor alpha (TGF-alpha), by the same tumor cells resulting inreceptor activation by an autocrine stimulatory pathway. Baselga and Mendelsohn Pharmac. Ther. 64:127-154 (1994). Monoclonal antibodies directed against the EGFR or its ligands, TGF-alpha and EGF, have been evaluated as therapeutic agents in the treatment of such malignancies. See, e.g., Baselga and Mendelsohn., supra; Masui et al. Cancer Research 44:1002-1007 (1984); and Wu et al. J. Clin. Invest. 95:1897-1905 (1995).

The second member of the ErbB family, p185neu, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., Science, 235:177-182 (1987); Slamon et al., Science, 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder.

Antibodies directed against the rat p185neu and human HER2 protein products have been described. Drebin and colleagues have raised antibodies against the rat neu gene product, p185neu (see, for example, Drebin et al., Cell 41:695-706 (1985); Myers et al., Meth. Enzym. 198:277-290 (1991); and WO94/22478). Drebin et al. (Oncogene 2:273-277 (1988)) report that mixtures of antibodies reactive with two distinct regions of p185neu result in synergistic anti-tumor effects on neu-transformed NIH-3T3 cells implanted into nude mice (see also U.S. Pat. No. 5,824,311).

Hudziak et al., (Mol. Cell. Biol. 9(3):1165-1172 (1989)) describe the generation of a panel of anti-HER2 antibodies, which were characterized using the human breast tumor cell line SKBR3. Relative cell proliferation of the SKBR3 cells following exposure to the antibodies was determined by crystal violet staining of the monolayers after 72 hours. Using this assay, maximum inhibition was obtained with the antibody called 4D5, which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-alpha (see, also, U.S. Pat. No. 5,677,171). The anti-HER2 antibodies discussed in Hudziak et al. were further characterized (Fendly et al. Cancer Research 50:1550-1558 (1990); Kotts et al. In Vitro 26(3): 59A (1990); Sarup et al. Growth Regulation 1:72-82 (1991); Shepard et al. J. Clin. Immunol. 11(3):117-127 (1991); Kumar et al. Mol. Cell. Biol. 11(2):979-986 (1991); Lewis et al. CancerImmunol. Immunother. 37:255-263 (1993); Pietras et al. Oncogene 9:1829-1838 (1994); Vitetta et al. Cancer Research 54:5301-5309 (1994); Sliwkowski et al. J. Biol. Chem. 269(20):14661-14665 (1994); Scott et al. J. Biol. Chem. 266:14300-5 (1991); D'souza et al. Proc. Natl. Acad. Sci. 91:7202-7206 (1994); Lewis et al. Cancer Research 56:1457-1465 (1996); and Schaefer et al. Oncogene 15:1385-1394 (1997)).

A recombinant humanized IgG1 version of the murine anti-HER2 antibody 4D5 (rhuMAb HER2 or HERCEPTIN®; commercially available from Genentech, Inc., South San Francisco) is clinically active in patients with HER2-overexpressing metastatic breast cancers that have received extensive prior anti-cancer therapy (Baselga et al., J. Clin. Oncol. 14:737-744 (1996)). HERCEPTIN® received marketing approval from the Food and Drug Administration Sep. 25, 1998 for the treatment of patients with metastatic breast cancer whose tumors overexpress the HER2 protein. The current treatment protocol employs IHC to determine HER2 protein overexpression.

Other anti-HER2 antibodies with various properties have been described (Tagliabue et al., Int. J. Cancer 47:933-937 (1991); McKenzie et al., Oncogene 4:543-548 (1989); Maier et al., Cancer Res. 51:5361-5369 (1991); Bacus et al., Molecular Carcinogenesis 3:350-362 (1990); Stancovski et al., (Proc. Natl. Acad. Sci. USA) 88:8691-8695 (1991); Bacus et al., Cancer Research 52:2580-2589 (1992); Xu et al. Int. J. Cancer 53:401-408 (1993); PCT Publication No. WO94/00136; Kasprzyk et al., Cancer Research 52:2771-2776 (1992); Hancock et al., Cancer Res. 51:4575-4580 (1991); Shawver et al., Cancer Res. 54:1367-1373 (1994); Arteaga et al. Cancer Res. 54:3758-3765 (1994); Harwerth et al., J. Biol. Chem. 267:15160-15167 (1992); U.S. Pat. No. 5,783,186; Klapper et al. Oncogene 14:2099-2109 (1997); and PCT Publication No. WO 98/17797).

Homology screening has resulted in the ErbB receptor family members: HER3 (U.S. Pat. Nos. 5,183,884 and 5,480,968; Kraus et al., Proc. Natl. Acad. Sci. USA 86:9193-9197 (1989)) and HER4 (European Patent Application No. EP 599 274; Plowman et al., Proc. Natl. Acad. Sci. USA, 90:1746-1750 (1993); and Plowman et al., Nature, 366:473-475 (1993)). Both of these receptors display increased expression on at least some breast cancer cell lines.

The ErbB receptors are generally found in various combinations in cells and heterodimerization is thought to increase the diversity of cellular responses to a variety of ErbB ligands (Earp et al., Breast Cancer Research and Treatment 35: 115-132 (1995)). EGFR is bound by six different ligands: Epidermal Growth Factor (EGF), Transforming Growth Factor-alpha (TGF-alpha), amphiregulin, Heparin Binding Epidermal Growth Factor (HB-EGF), betacellulin, and epiregulin (Groenen et al. GrowthFactors 11:235-257 (1994)). A family of heregulin proteins resulting from alternative splicing of a single gene are ligands for HER3 and HER4. The heregulin family includes alpha, beta, and gamma heregulins (Holmes et al., Science, 256:1205-1210 (1992); U.S. Pat. No. 5,641,869; and Schaefer et al., Oncogene 15:1385-1394 (1997)); neu differentiation factors (NDFs), glial growth factors (GGFs); acetylcholine receptor inducing activity (ARIA); and sensory and motorneuron derived factor (SMDF) (for a review, see Groenen et al., Growth Factors 11:235-257 (1994); Lemke, G. Molec. & Cell. Neurosci. 7:247-262 (1996) and Lee et al. Pharm. Rev. 47:51-85 (1995)). Recently, two additional ErbB ligands were identified: neuregulin-2 (NRG-2), which is reported to bind either HER3 or HER4 (Chang et al., Nature: 387 509-512 (1997); and Carraway et al Nature 387:512-516 (1997)) and neuregulin-3, which binds HER4 (Zhang et al., (Proc. Natl. Acad. Sci. USA) 94(18): 9562-7 (1997)). HB-EGF, betacellulin, and epiregulin also bind to HER4.

While EGF and TGF-alpha do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase, (Earp et al., supra.) Likewise, when HER3 is co-expressed with HER2, an active signaling complex is formed and antibodies directed against HER2 are capable of disrupting this complex (Sliwkowski et al., J. Biol. Chem., 269(20):14661-14665 (1994)). Additionally, the affinity of HER3 for heregulin (HRG) is increased to a higher affinity state when co-expressed with HER2. See also, Levi et al., Journal of Neuroscience15: 1329-1340 (1995); Morrissey et al., Proc. Natl. Acad. Sci. USA 92:1431-1435 (1995); and Lewis et al., Cancer Res., 56:1457-1465 (1996) with respect to the HER2-HER3 protein complex. HER4, like HER3, forms an active signaling complex with HER2 (Carraway and Cantley, Cell 78:5-8 (1994)).

Detecting Gene Amplification

The present invention contemplates using any technique to detect gene amplification. (see, Boxer, J. Clin. Pathol. 53: 19-21 (2000)). These techniques include in situ hybridization (Stoler, Clin. Lab. Med. 12:215-36 (1990), using radioisotope or fluorophore-labeled probes; polymerase chain reaction (PCR); quantitative Southern blotting, and other techniques for quantitating individual genes. Preferably probes or primers selected for gene amplification evaluation are highly specific, to avoid detecting closely related homologous genes.

The word "label" when used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition which is detectable. A hapten or epitope that is immunospecifically bound by an antibody can also serve as a label.

The term "fluorescently labeled nucleic acid probe" refers to a probe comprising (1) a nucleic acid having a sequence rendering it capable of hybridizing with a target nucleic acid sequence and (2) a fluorescent label. Preferably such hybridization is specific, i.e., it can occur under high stringency conditions.

Sample Preparation

Any tissue sample from a subject may be used. Examples of tissue samples that may be used include, but are not limited to, breast, prostate, ovary, colon, lung, endometrium, stomach, salivary gland or pancreas. The tissue sample can be obtained by a variety of procedures including, but not limited to surgical excision, aspiration, or biopsy. The tissue may be fresh or frozen. In one embodiment, the tissue sample is fixed and embedded in paraffin or the like.

The tissue sample may be fixed (i.e., preserved) by conventional methodology (See e.g., *Manual of Histological Staining Method of the Armed Forces Institute of Pathology,* 3$^{rd}$ *Edition* Lee G. Luna, H T (ASCP) Editor, The Blakston Division McGraw-Hill Book Company: New York; (1960); *The Armed Forces Institute of Pathology Advanced Laboratory Methods in Histology and Pathology* (1994) Ulreka V. Mikel, Editor, Armed Forces Institute of Pathology, American Registry of Pathology, Washington, D.C.). One of skill in the art will appreciate that the choice of a fixative is determined by the purpose for which the tissue is to be histologically stained or otherwise analyzed. One of skill in the art will also appreciate that the length of fixation depends upon the size of the tissue sample and the fixative used. By way of example, neutral buffered formalin, Bouin's or paraformaldehyde, may be used to fix a tissue sample.

Generally, the tissue sample is first fixed and is then dehydrated through an ascending series of alcohols, infiltrated, and embedded with paraffin or other sectioning media so that the tissue sample may be sectioned. Alternatively, one may section the tissue and fix the sections obtained. By way of example, the tissue sample may be embedded and processed in paraffin by conventional methodology. Examples of paraffin that may be used include, but are not limited to, Paraplast, Broloid, and Tissuemay. Once the tissue sample is embedded, the sample may be sectioned by a microtome or the like. By way of example for this procedure, sections may range from about three microns to about five microns in thickness. Once sectioned, the sections may be attached to slides by several standard methods. Examples of slide adhesives include, but are not limited to, silane, gelatin, poly-L-lysine, and the like. For example, the paraffin embedded sections may be attached to positively charged slides, slides coated with poly-L-lysine.

If paraffin has been used as the embedding material, the tissue sections are generally deparaffinized and rehydrated to water. The tissue sections may be deparaffinized by several conventional standard methodologies. For example, xylenes and a gradually descending series of alcohols may be used. Alternatively, commercially available deparaffinizing non-organic agents such as Hemo-De7 (CMS, Houston, Tex.) may be used.

Fluorescence In Situ Hybridization (FISH)

In situ hybridization is generally carried out on cells or tissue sections fixed to slides. In situ hybridization may be performed by several conventional methodologies (see, e.g., Leitch et al., *In Situ Hybridization: A Practical Guide,* Oxford BIOS Scientific Publishers, Micropscopy Handbooks v. 27 (1994)). In one in situ procedure, fluorescent dyes (such as fluorescein isothiocyanate (FITC) which fluoresces green when excited by an Argon ion laser) are used to label a nucleic acid sequence probe that is complementary to a target nucleotide sequence in the cell. Each cell containing the target nucleotide sequence will bind the labeled probe producing a fluorescent signal upon exposure, of the cells to a light source of a wavelength appropriate for excitation of the specific fluorochrome used. A "target nucleotide sequence" is a sequence specific for a over-expressed tumor antigen, such as ErbB. FISH analysis can be used in conjunction with other assays, including without limitation morphological staining (of serial sections or the same section; see PCT Publication No. WO 00/20641, specifically incorporated herein by reference).

Various degrees of hybridization stringency can be employed. As the hybridization conditions become more stringent, a greater degree of complementarity is required between the probe and target to form and maintain a stable duplex. Stringency is increased by raising temperature, lowering salt concentration, or raising formamide concentration. Adding dextran sulfate or raising its concentration may also increase the effective concentration of labeled probe to increase the rate of hybridization and ultimate signal intensity. After hybridization, slides are washed in a solution generally containing reagents similar to those found in the hybridization solution with washing time varying from minutes to hours depending on required stringency. Longer or more stringent washes typically lower nonspecific background but run the risk of decreasing overall sensitivity.

Probes used in the FISH analysis may be either RNA or DNA oligonucleotides or polynucleotides and may contain not only naturally occurring nucleotides but their analogs like digoxygenin dCTP, biotin dcTP 7-azaguanosine, azidothymidine, inosine, or uridine. Other useful probes include peptide probes and analogues thereof, branched gene DNA, peptidometics, peptide nucleic acid (PNA), and/or antibodies.

Probes should have sufficient complementarity to the target nucleic acid sequence of interest so that stable and specific binding occurs between the target nucleic acid sequence and the probe. The degree of homology required for stable hybridization varies with the stringency of the hybridization medium and/or wash medium. Preferably, completely homologous probes are employed in the present invention, but persons of skill in the art will readily appreciate that probes exhibiting lesser but sufficient homology can be used in the present invention (see e.g., Sambrook, J., et al., *Molecular Cloning A Laboratory Manual,* Cold Spring Harbor Press, (1989)).

One of skill in the art will appreciate that the choice of probe depends on the characteristics of the target gene of interest. Examples of amplification include, but are not limited to, her2/neu in breast and ovarian cancer, n-myc in neuroblastoma, c-myc in small cell lung cancer. By way of example for evaluating her2/neu amplification a probe spanning a 140 kb region on the long arm of chromosome 17 containing the her2/neu gene (17q 11.2-17q12) may be used. A probe for the -satellite sequences in the centromeric region of chromosome 17(D1721) may be used to evaluate for aneusomy of chromosome 17 as a source or cause for her2/neu amplification. For example, a cocktailed version of these probes may be obtained from Vysis, Inc. where each probe is directly labeled with easily distinguishable fluorophores, such as SPECTRUM ORANGE® and SPECTRUM GREEN®.

Probes may also be generated and chosen by several means including, but not limited to, mapping by in situ hybridization, somatic cell hybrid panels, or spot blots of sorted chromosomes; chromosomal linkage analysis; or cloned and isolated from sorted chromosome libraries from human cell lines or somatic cell hybrids with human chromosomes, radiation somatic cell hybrids, microdissection of a chromosome region, or from yeast artificial chromosomes (YACs) identified by PCR primers specific for a unique chromosome locus or other suitable means like an adjacent YAC clone. Probes may be genomic DNA, cDNA, or RNA cloned in a plasmid, phage, cosmid, YAC, Bacterial Artificial Chromosomes (BACs), viral vector, or any other suitable vector. Probes may be cloned or synthesized chemically by conventional methods. When cloned, the isolated probe nucleic acid fragments are typically inserted into a vector, such as lambda phage, pBR322, M13, or vectors containing the SP6 or T7 promoter and cloned as a library in a bacterial host (see, e.g., Sambrook, supra).

Probes are preferably labeled with a fluorophor. Examples of fluorophores include, but are not limited to, rare earth chelates (europium chelates), Texas Red, rhodamine, fluorescein, dansyl, Lissamine, umbelliferone, phycocrytherin, phycocyanin, or commercially available fluorophors such SPECTRUM ORANGE® and SPECTRUM GREEN®, and/or derivatives of any one or more of the above. Multiple probes used in the assay may be labeled with more than one distinguishable fluorescent or pigment color. These color differences provide a means to identify the hybridization positions of specific probes. Moreover, probes that are not separated spatially can be identified by a different color light or pigment resulting from mixing two other colors (e.g., light red+ green=yellow), pigment (e.g., blue+yellow=green), or by using a filter set that passes only one color at a time.

Probes can be labeled directly or indirectly with the fluorophor, utilizing conventional methodology. Additional probes and colors may be added to refine and extend this general procedure to include more genetic abnormalities or serve as internal controls. By way of example the her2/neu gene is in chromosome 17, and as an internal control a probe for satellite sequences specific for chromosome 17 (D17Z1) may be used (Vysis, Inc.) to prove diploidy in areas of non-malignant cells and/or to establish the presence or absence of chromosome 17 aneusomy in areas of her2/neu amplification.

After processing for FISH, the slides may be analyzed by standard techniques of fluorescence microscopy (see, e.g., Ploem and Tanke, Introduction to Fluorescence Microscopy, Oxford University Press: New York (1987)). Briefly, each slide is observed using a microscope equipped with appropriate excitation filters, dichromic, and barrier filters. Filters are chosen based on the excitation and emission spectra of the fluorochromes used. Photographs of the slides may be taken with the length of time of film exposure depending on the fluorescent label used, the signal intensity and the filter chosen. For FISH analysis the physical loci of the cells of interest determined in the morphological analysis are recalled and visually conformed as being the appropriate area for FISH quantification.

In order to correlate IHC with FISH, one may use a computer-driven, motorized stage which stores location of co-ordinates. This may be used to evaluate the same area by two different analytical techniques. For example, color images of the morphologically stained areas may be captured and saved using a computer-assisted cooled CCD camera. The same section may be subsequently taken through the FISH procedure, the stored locations recalled, and the designated areas scored for the presence of fluorescent nuclear signals. A similar procedure for IHC followed by FISH is contemplated.

Typically, hundreds of cells are scanned in a tissue sample and quantification of the specific target nucleic acid sequence is determined in the form of fluorescent spots, which are counted relative to the number of cells. Deviation of the number of spots in a cell from a norm (e.g., such as probing for the her2/neu gene in a normal cell will produce two copies, abnormal greater than two) is indicative of a greater likelihood of benefit from a tumor antigen-specific antibody therapy, e.g., an ErbB antagonist therapy. As exemplified infra, her2 gene amplification provides a much more effective indication of the likelihood that an anti-HER2 antibody therapy will be effective.

Pharmaceutical Formulations

Therapeutic formulations of the antagonists, e.g., antibodies, used in accordance with the present invention are prepared for storage by mixing an antibody having the desired degree of purity with optional pharmaceutically acceptable carriers, excipients or stabilizers (*Remington's Pharmaceutical Sciences* 17th edition, Osol, A. Ed.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Preferred lyophilized anti-ErbB2 antibody formulations are described in WO 97/04801, expressly incorporated herein be reference.

The formulation herein may also contain more than one active compound as necessary for the particular indication being treated, preferably those with complementary activities that do not adversely affect each other. For example, it may be desirable to further provide antibodies which bind to EGFR, ErbB2, ErbB3, ErbB4, vascular endothelial factor (VEGF), or an antibody that binds to a different epitope on the target ErbB, in the one formulation. Alternatively, or in addition, the composition may comprise a cytotoxic agent, a chemotherapeutic, a cytokine, growth inhibitory agent and/or cardioprotectant. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 17th edition, Osol, A. Ed.

The formulations to be used for in vivo administration are preferably, and in the case of humans, must be, sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Treatment with the Anti-ErbB Antagonists

It is contemplated that, according to the present invention, the anti-ErbB antibodies or other antagonists may be used to treat various conditions characterized by overexpression and/or activation of the ErbB receptor in patients who have been found to have an amplified erbB gene. Exemplary conditions or disorders include benign or malignant tumors (e.g. renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic, glandular, macrophagal, epithelial, stromal, blastocoelic, inflammatory, angiogenic and immunologic disorders.

The antibodies, chemotherapeutic agents and any other active agents of the invention are administered to a human patient in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous or subcutaneous administration of the antibody is preferred.

In one embodiment, the treatment of the present invention involves the combined administration of an anti-ErbB antibody and a chemotherapeutic agent, e.g., a taxoid. The present invention contemplates administration of cocktails of different chemotherapeutic agents. The combined administration includes coadministration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antibody or may be given simultaneously therewith. The antibody may be combined with an anti-estrogen compound such as tamoxifen or an anti-progesterone such as onapristone (see, EP 616 812) in dosages known for such molecules.

In addition to the above therapeutic regimes, the patient may be subjected to surgical removal of cancer cells (tumor resection) and/or radiation therapy.

For the prevention or treatment of disease, the appropriate dosage of antagonist, e.g., antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 µg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Pharmaceutical Packages

Articles of Manufacture

In a related aspect of the invention, an article of manufacture containing materials useful for the treatment of the disorders described above is provided. The article of manufacture comprises a container, optionally labeled, and a package insert. Suitable containers include, for example, bottles, vials, syringes, etc. The containers may be formed from a variety of materials, such as glass or plastic. The container holds a composition that is effective for treating the condition and preferably has a sterile access port (for example the container may be an intravenous solution bag or a vial having a stopper pierceable by a hypodermic injection needle). At least one active agent in the composition is an anti-tumor antigen therapeutic antibody or an ErbB antagonist, e.g., an anti-ErbB antibody. A label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. This second buffer can be used to reconstitute the active agent, if that is provided as a lyophilysate or dried powder, or to dilute a concentrated preparation of the active agent. It may further include other materials desirable from a commercial and user standpoint, including other buffers, diluents, filters, needles, and syringes.

In addition, the article of manufacture comprises a package insert or inserts with instructions for use in patients who have been found to have erbB gene amplification, e.g., by FISH testing. Such patients may be subjects who, by IHC, would be excluded from treatment with the ErbB antagonist, e.g., patients who score a 0 or 1+ using an anti-HER2 antibody.

Deposit of Materials

The following hybridoma cell lines have been deposited with the American Type Culture Collection, 12301 Parklawn Drive, Rockville, Md., USA (ATCC):

| Antibody Designation | ATCC No. | Deposit Date |
| --- | --- | --- |
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |

Further details of the invention are illustrated by the following non-limiting Examples.

Example 1

Concordance Between the Clinical Trials Assay (CTA) and Fluorescence In Situ Hybridization (FISH) in the HERCEPTIN® Pivotal Trials Overexpression of HER2 at the 2+ or 3+ level by immunohistochemistry (IHC) was required for enrollment in the pivotal HERCEPTIN® metastatic breast cancer trials. The Clinical Testing Assay (CTA) involves two separate IHC assays performed with either monoclonal antibodies 4D5 (after protease digestion of the formalin fixed sample) or CB11 (after heat treatment of the formalin fixed sample). Subjects were eligible if either assay was scored at 2+ or 3+. If both were performed, the final score was the higher of the two results.

Concordance between the CTA and another IHC, HERCEPTEST® (HT), is 79%. This was the basis for FDA approval of HT to aid in the selection of patients for HERCEPTIN® therapy.

This Example describes a similar concordance study, utilizing clinical material submitted for screening for the HERCEPTIN® pivotal trials, that compares the CTA to her2/neu gene amplification measured by the PathVysion FISH assay. In the pivotal trials, 5998 subjects were screened for HER2 expression; 1915 (32%) were positive by the CTA and 4083 (68%) were negative. A random sample of 623 specimens (1:1 ratio of positive:negative) were selected for this analysis, 317 CTA+ and 306 CTA−. Specimens were not freshly cut from blocks. They had been stored between 2 and 4 years as 4-6µ sections on glass slides. Each section was assayed for her2/neu amplification using the protocol specified in the package insert of the PathVysion assay. Amplification was defined as a signal ratio of greater than or equal to 2. The results are shown in Table 1.

TABLE 1

FISH/CTA Concordance

| | | CTA | | | |
|---|---|---|---|---|---|
| | | 0 | 1+ | 2+ | 3+ |
| FISH | − | 207 | 28 | 67 | 21 |
| | + | 7 | 2 | 21 | 176 |
| | | 4% | 7% | 24% | 89% | 529 |

FISH+ = HER2:CEP17 signal ratio ≧2
Concordance = 82% (79-85%)

For the total 623 specimens tested, a FISH signal result was obtained in 529. Assay failure occurred in 19.9% of CTA− and 10.4% CTA+ samples. Amplification in the 0, 1+, 2, and 3+ groups was 4.2%, 6.7%, 23.9%, and 89.3%, respectively. The sample concordance was 81.3%, similar to the CTA/HT concordance of 79%. Single copy overexpression was 31%, predominantly in the 2+ group. Amplification was rarely (4.6%) noted in the CTA− group. The higher assay failure rate in the CTA− group may be due to non-assay related factors such as tissue fixation. These may have also resulted in false negative results for IHC.

These data were closely interpreted to suggest that her2/neu amplification status may have unexpectedly superior predictive value for identifying patients who are more likely to benefit from HERCEPTIN® treatment as compared to HERCEPTEST®. The observation that only 24% of 2+ patients are FISH+ suggest that this sub-group may have less predictable treatment outcomes when selected by IHC only. Identification of FISH+ patients in the 1+ and 0 sub-groups might identify subjects who, though failing the IHC criteria for HERCEPTIN® treatment, would likely benefit from HERCEPTIN® treatment. A direct analysis of HERCEPTIN® benefit based on FISH score compared to IHC score is presented in Example 2.

Example 2

FISH/Clinical Outcome Study

This example links the results from three HERCEPTIN® Trials with FISH status. In this study, 805 subjects were selected at random from all three trials. Of these, 167 lacked slides. Another 78 assays (9.7%) failed. Thus, formalin-fixed cut sections stored between 2.5 and 4.5 years from 540 subjects provided the sample pool for this study. There were no imbalances in demographics or prognostic indicators in these samples. Results are reported for different treatment groups.

Correlation of FISH status with response was evaluated for patients who received HERCEPTIN® as a second or third line therapy. These data are reported for 2+ and 3+ (by CTA) subjects in Table 2.

TABLE 2

FISH/Response with single agent HERCEPTIN ®, 2nd or 3rd line therapy, 2+/3+ Combined

| | FISH+ | FISH− |
|---|---|---|
| Response | 21 | 0 |
| No response | 84 | 37 |
| response rate | 20% | 0% |
| | (12.5-27.5%) | (0.7%) |

N = 142

The 20% response rate of FISH+ subjects unexpectedly exceeds the 15% response rate of 2+ and 3+ patients in this study and 14% response rate observed in patients selected by CTA with a 2+ or 3+ immunohistochemistry score during the pivotal trials. Thus, while FISH correlates well with NC to about the same degree as another NC assay, the Hercep Test, as shown in Example 1, it unexpectedly is superior in identifying patients who are more likely to benefit from HERCEPTIN® therapy.

When these data were broken down into the components 3+ and 2+ subjects, the same 20% response rate of FISH+ subjects was seen (Tables 3 and 4).

TABLE 3

FISH/Response with single agent HERCEPTIN ®, 2nd or 3rd line therapy, 3+ subgroup

| | FISH+ | FISH− |
|---|---|---|
| Response | 18 | 0 |
| No response | 72 | 17 |
| response rate | 20% | 0% |
| | (12-28%) | (0-14%) |

N = 107

TABLE 4

FISH/Response with single agent HERCEPTIN ®,
2nd or 3rd line therapy, 2+ subgroup

|  | FISH+ | FISH− |
|---|---|---|
| Response | 3 | 0 |
| No response | 12 | 20 |
| response rate | 20% | 0% |
|  | (1-40%) | (0-14%) |

N = 35

In the 3+ sub-group, the FISH+ response rate (20%) was very close but still exceeded the 17% response rate of 3+ subjects. The 2+ subgroup showed a much greater difference, with only a 9% response rate versus 20% by FISH+ selection. These data show that FISH+ status (her2 gene amplification) greatly increases the likelihood of response to HERCEPTIN®.

Data were also evaluated for patient responses to HERCEPTIN® as a first line therapy (Table 5).

TABLE 5

FISH/Response with single agent HERCEPTIN ® as
1st line therapy, 2+/3+ combined

|  | FISH+ | FISH− |
|---|---|---|
| Response | 17 | 1 |
| No response | 24 | 20 |
| response rate | 41% | 20% |
|  | (26-56%) | (0-14%) |

N = 62

The 41% response rate of FISH+ subjects was notably greater than the 27% response rate of 3+, 2+ subjects.

The surprising increase in likelihood of beneficial response based on FISH analysis extended to responses to chemotherapy plus HERCEPTIN®, as shown in Table 6. FISH+ subjects showed a much greater response to chemotherapy and HERCEPTIN® (54%) than FISH−(41%). Tables 7-9 contain more extensive data, broken down by different chemotherapeutic agents (adrinomycin and cyclophosphamide, AC; and Paditaxol, P) and different endpoints (response rate, time to progression, and survival) for HERCEPTIN® in combination with chemotherapy.

TABLE 6

FISH/Response rate to chemotherapy +/− HERCEPTIN ®, 1st
line therapy; 2+/3+ combined

|  | C alone | C + H |
|---|---|---|
| FISH− | 39% | 41% |
|  | (26-52%) | (27-55%) |
| FISH+ | 27% | 54% |
|  | (19-35%) | (45-63%) |

N = 336

TABLE 7

Response rate of newly defined populations

|  |  | H + Ac (n = 143) | AC (n = 138) | H + P (n = 92) | P (n = 96) | H + CT (n = 235) | CT (n = 234) |
|---|---|---|---|---|---|---|---|
| 2+/3+ | 469 | 56* | 42 | 41* | 17 | 50* | 32 |
| 3+ | 349 | 60* | 42 | 49* | 17 | 56* | 31 |
| FISH+ | 240 | 58* | 40 | 49* | 14 | 54* | 27 |

*p < 0.05

TABLE 8

Time to progression (months) of newly defined populations

|  |  | H + Ac (n = 143) | AC (n = 138) | H + P (n = 92) | P (n = 96) | H + CT (n = 235) | CT (n = 234) |
|---|---|---|---|---|---|---|---|
| 2+/3+ | 469 | 7.8* | 6.1 | 6.9* | 2.7 | 7.4* | 4.6 |
| 3+ | 349 | 8.1* | 6.0 | 7.1* | 3.0 | 7.8* | 4.6 |
| FISH+ | 240 | 7.8* | 6.2 | 7.0* | 3.2 | 7.3* | 4.6 |

*p < 0.05

TABLE 9

Survival (months) of newly defined populations

|  |  | H + Ac (n = 143) | AC (n = 138) | H + P (n = 92) | P (n = 96) | H + CT (n = 235) | CT (n = 234) |
|---|---|---|---|---|---|---|---|
| 2+/3+ | 469 | 27 | 21 | 22 | 18 | 25* | 20 |
| 3+ | 349 | 31* | 21 | 25 | 18 | 29* | 20 |
| FISH+ | 240 | 29* | 20 | 25* | 14 | 27* | 18 |

*p < 0.05

These data uniformly confirm that FISH+ analysis, though correlating closely to IHC, provides a much more accurate indicator of likelihood of success with HERCEPTIN® treatment. Across the board, FISH+ selection has about ⅓ (30%) greater response rate than 2+/3+ IHC-selection. When focused on 2+ patients, FISH status provides a much more effective tool for patient selection. FISH states also identifies patients who, because of 0 or 1+ status as determined by IHC, would otherwise be excluded from treatment.

These observations have broad implications for ErbB receptor antagonist-based cancer therapies and anti-tumor antigen cancer therapies in general. Thus erbB antagonists, e.g., anti-erbB receptor antibodies like HERCEPTIN®, can have an increased likelihood of efficacy when administered to patients who are positive for erbB gene amplification, e.g., by a FISH test. This is certainly the case, based on these data, with HERCEPTIN®.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method for identifying and treating a patient disposed to respond favorably to a HER2 antibody, huMAb4D5-8, for treating breast cancer, which method comprises detecting her2 gene amplification in tumor cells in a tissue sample from the patient and treating the patient with her2 gene amplification with the HER2 antibody in an amount effective to treat the breast cancer, wherein the patient's tumor cells express HER2 at a 0 or 1+ level by immunohistochemistry.

2. The method of claim 1 wherein her2 gene amplification is detected by detecting fluorescence of a fluorescent-labeled nucleic acid probe hybridized to the gene.

3. The method of claim 1 wherein a formaldehyde-fixed sample of the patient's tumor cells has been subjected to an immunohistochemistry assay and found to express HER2 at a 0 or 1+ level.

4. The method of claim 3 wherein the immunohistochemistry assay is performed prior to detecting her2 gene amplification.

5. The method of claim 1 which further comprises administering a cancer treating dose of a chemotherapeutic drug.

6. The method of claim 5 wherein the chemotherapeutic drug is a taxoid.

* * * * *